(12) United States Patent
Song et al.

(10) Patent No.: US 10,386,530 B2
(45) Date of Patent: Aug. 20, 2019

(54) NMR PROBE AND METHODS OF USE

(71) Applicant: SCHLUMBERGER TECHNOLOGY CORPORATION, Sugar Land, TX (US)

(72) Inventors: Yi-Qiao Song, Newton Center, MA (US); Soumyajit Mandal, Cleveland, OH (US); Yiqiao Tang, Chongqing (CN); Martin D. Hurlimann, Newton, MA (US); Jeffrey Paulsen, Brookline, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 1126 days.

(21) Appl. No.: 14/431,843

(22) PCT Filed: Sep. 27, 2013

(86) PCT No.: PCT/US2013/062194
§ 371 (c)(1),
(2) Date: Mar. 27, 2015

(87) PCT Pub. No.: WO2014/052762
PCT Pub. Date: Apr. 3, 2014

(65) Prior Publication Data
US 2015/0253454 A1    Sep. 10, 2015

Related U.S. Application Data

(60) Provisional application No. 61/707,614, filed on Sep. 28, 2012.

(51) Int. Cl.
*G01R 33/30* (2006.01)
*G01V 3/32* (2006.01)
(Continued)

(52) U.S. Cl.
CPC .............. *G01V 3/32* (2013.01); *E21B 49/088* (2013.01); *G01N 24/081* (2013.01);
(Continued)

(58) Field of Classification Search
CPC ...... G01V 3/32; E21B 49/088; G01R 33/307; G01R 33/345; G01R 33/448;
(Continued)

(56) References Cited

U.S. PATENT DOCUMENTS

| 4,116,836 | A | 9/1978 | DeAngelis |
| 5,045,793 | A | 9/1991 | Rathke |

(Continued)

FOREIGN PATENT DOCUMENTS

| EP | 1918730 A1 | 5/2008 | |
| JP | 03108680 A | * 5/1991 | ............. G01R 33/30 |
| JP | H03108680 A | 5/1991 | |

OTHER PUBLICATIONS

J-Plat Pat translation Mar. 12, 2018 of JP03108680A.*
(Continued)

*Primary Examiner* — Melissa J Koval
*Assistant Examiner* — Courtney G McDonnough

(57) ABSTRACT

A coaxial nuclear magnetic resonance (NMR) probe and related methods are described herein. The coaxial NMR probe includes a housing with a fluid inlet, a fluid outlet, a longitudinal axis, and an interior volume. The housing contains a fluid sample that is analyzed by the probe. The coaxial NMR probe also includes an elongated conductor disposed along the longitudinal axis of the housing. The elongated conductor generates an oscillating electromagnetic field within the interior volume of the housing. The oscillating electromagnetic field produces a NMR signal within the fluid sample. The elongated conductor may also be used to receive this NMR signal. The NMR signal is then
(Continued)

analyzed to determine information about the fluid sample. Various NMR pulse sequences for use with this coaxial probe and other coaxial probes are also described herein.

23 Claims, 14 Drawing Sheets

(51) Int. Cl.

| | | |
|---|---|---|
| *E21B 49/08* | (2006.01) | |
| *G01N 24/08* | (2006.01) | |
| *G01R 33/345* | (2006.01) | |
| G01R 33/44 | (2006.01) | |
| G01R 33/46 | (2006.01) | |
| G01N 24/10 | (2006.01) | |
| G01R 33/383 | (2006.01) | |

(52) U.S. Cl.
CPC ......... *G01R 33/307* (2013.01); *G01R 33/345* (2013.01); *G01N 24/10* (2013.01); *G01R 33/383* (2013.01); *G01R 33/448* (2013.01); *G01R 33/4608* (2013.01); *G01R 33/4633* (2013.01)

(58) Field of Classification Search
CPC ............ G01R 33/4608; G01R 33/4633; G01R 33/383; G01N 24/081; G01N 24/10
USPC .................................................. 324/321, 309
See application file for complete search history.

(56) References Cited

U.S. PATENT DOCUMENTS

| | | | | |
|---|---|---|---|---|
| 5,574,370 | A * | 11/1996 | Woelk .................. | G01R 33/343 324/318 |
| 5,986,453 | A * | 11/1999 | Anderson ........ | G01R 33/34053 324/300 |
| 6,046,592 | A | 4/2000 | Rathke et al. | |
| 6,538,444 | B2 | 3/2003 | Gerald, II et al. | |
| 6,674,283 | B2 | 1/2004 | Gerald, II et al. | |
| 6,788,064 | B2 | 9/2004 | Gerald, II et al. | |
| 6,791,326 | B2 | 9/2004 | Gerald, II et al. | |
| 7,268,552 | B1 | 9/2007 | Gerald, II et al. | |
| 2004/0108852 | A1 | 6/2004 | de Swiet | |
| 2009/0066330 | A1* | 3/2009 | Cheng .................... | G01N 24/08 324/315 |
| 2012/0049844 | A1 | 3/2012 | Leveridge et al. | |
| 2012/0169334 | A1* | 7/2012 | Hopper ................ | G01N 24/081 324/303 |

OTHER PUBLICATIONS

Ardelean, I. et al., "Principles and Unconventional Aspects of NMR Diffusometry", Annual Reports on NMR Spectroscopy, 2003, 49, pp. 43-110.
Canet, D. et al., "Self-Diffusion Measurements Using a Radiofrequency Field Gradient", Journal of Magnetic Resonance,1989, 81(1), pp. 1-12.
Canet , D., "Radiofrequency Field Gradient Experiments", Progress in Nuclear Magnetic Resonance Spectroscopy, 1997, 30(1-2), pp. 101-135.
Freed, D. E. et al., "Molecular Composition and Dynamics of Oils from Diffusion Measurements", Asphaltenes, Heavy Oils, and Petroleomics, 2007, pp. 279-299.
Freed, D. E. et al., "Scaling Laws for Diffusion Coefficients in Mixtures of Alkanes", Physical Review Letters, 2005, 94(6), 67602, pp. 1-4.
Han, H. et al., "High Pressure Magnetic Resonance Imaging with Metallic Vessels", Journal of Magnetic Resonance, 2011, 213, pp. 90-97.
Humbert, F. et al., "Diffusion Measurements Using Radiofrequency Field Gradient: Artifacts, Remedies, Practical Hints", Journal of Magnetic Resonance, 1998, 134(2), pp. 245-254.
Hürlimann , M. D. et al., "Quantitative Characterization of Food Products by Two-Dimensional D-T2 and T1-T2 Distribution Functions in a Static Gradient", Journal of Colloid Interface Science, 2006, 297(1), pp. 303-311.
Hürlimann, M. D. et al., "Quantitative Measurement of Two-Dimensional Distribution Functions of Diffusion and Relaxation in Grossly Inhomogeneous Fields", Journal of Magnetic Resonance, 2002, 157(1), pp. 31-42.
Hürlimann, M. D., "Diffusion and Relaxation Effects in General Stray Field NMR Experiments", Journal of Magnetic Resonance, 2001, 148(2), pp. 367-378.
Hürlimann, M.D., "Well Logging," Encyclopedia of Magnetic Resonance, 2012, pp. 1-10, John Wiley & Sons, Ltd.
Price, W. S., "Pulsed-field Gradient Nuclear Magnetic Resonance as a Tool for Studying Translational Diffusion: Part I. Basic Theory", Concepts in Magnetic Resonance, 1997, 9(5), pp. 299-336.
Song, Y. Q. et al., "TI-T2 Correlation Spectra Obtained Using a Fast Two-Dimensional Laplace Inversion", Journal of Magnetic Resonance, 2002, 154(2), pp. 261-268.
Tofts, P. et al., "Test Liquids for Quantitative MRI Measurements of Self-Diffusion Coefficient in Vivo", Magnetic Resonance in Medicine, 2000, 43(3), pp. 368-374.
Trautner, P. et al., "Improved Strategies for NMR Diffusion Measurements with Magnetization-grating Rotating-frame Imaging (MAG ROFI)", Physical Chemistry Chemical Physics, 2002, 4, pp. 5973-5981.
Trautner, P., "Angular Flow in Toroid Cavity Probes", Journal of Magnetic Resonance, 2001, 151(2), pp. 284-290.
Woelk, K. et al., "Imaging Diffusion in Toroid Cavity Probes", Journal of Magnetic Resonance, 1996, 121(1), pp. 74-77.
Woelk, K. et al., "The Toroid Cavity NMR Detector", Journal of Magnetic Resonance, Series A, 1994, 109(2), pp. 137-146.
International Search Report and Written Opinion of PCT Application No. PCT/US2013/062194 dated Jan. 24, 2014, pp. 1-14.
International Preliminary Report on Patentability of PCT application No. PCT/US2013/062194 dated Apr. 9, 2015.
Exam Report of European Patent Application No. 13841344.8 dated May 25, 2016, pp. 1-7.
R61-R63 Supplementary Search Report of European Patent Application No. 13841344.8 dated Apr. 28, 2016, pp. 1-4.

* cited by examiner

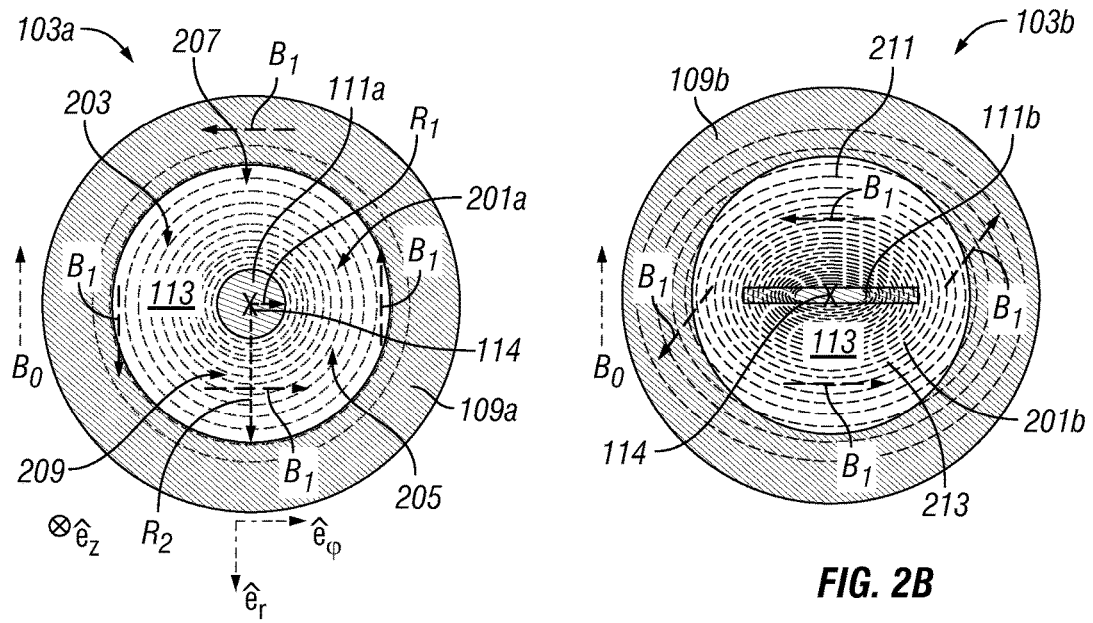
FIG. 2A
FIG. 2B
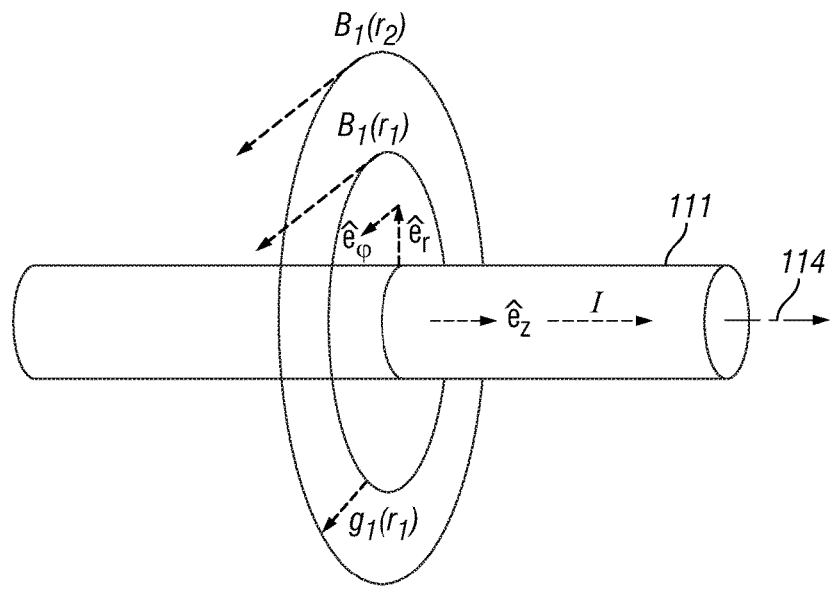
FIG. 2C

Inversion Recovery

Composite Rotary Echo-Spin Echo ph1 = x
ph2 = x -x
ph3 = x x -x -x y y -y -y
ph4 = y -y y -y x -x x -x
ph5 = x x -x -x y y -y -y

NMR PROBE AND METHODS OF USE

CROSS-REFERENCE TO RELATED APPLICATIONS

This application claims priority to U.S. Provisional Application No. 61/707,614, filed on Sep. 28, 2012, which is incorporated by reference herein in its entirety.

BACKGROUND

The oil and gas industry has developed various tools capable of determining formation fluid properties. For example, borehole fluid sampling and testing tools such as Schlumberger's Modular Formation Dynamics Tester (MDT™) tool can provide valuable information on the type and properties of reservoir fluids in addition to providing measurements of reservoir pressure, permeability, and mobility. These tools may perform measurements of the fluid properties downhole, using sensor modules on board the tools. Alternatively, these tools can withdraw fluid samples from the reservoir that can be collected in bottles and brought to the surface for analysis. The collected samples are routinely sent to fluid properties laboratories for analysis of physical properties that include, among other things, oil viscosity, gas-oil ratio, mass density or API gravity, molecular composition, $H_2S$, asphaltenes, resins, and various other impurity concentrations.

A number of different tools use nuclear magnetic resonance based methods and devices for making measurements in a borehole on fluid samples withdrawn from earth formations. For example, an NMR module on the flow line of the MDT tool may be used for determining different fluid properties from magnetic resonance signals.

Formation fluids often contain several components, each of which likely has a different diffusion property. Therefore, measurement of diffusion coefficients may provide valuable information on the formation fluid properties. Some NMR methods make use of magnetic field gradients to probe the diffusion properties of the formation fluids. For example, some tools are capable of making $T_1$ measurements on fluids flowing in the flowline of a fluid sampling tool. Furthermore, static gradient methods may be used for making diffusion measurements on stationary samples. However, this method of deriving the diffusion data from the NMR measurements assumes a single diffusion constant, despite it being well known that crude oils have a distribution of diffusion coefficients.

Other tools are capable of measuring the relaxation times ($T_1$ and $T_2$) and the diffusion coefficients (D) of fluids in an NMR module of a fluid sampling tool. For example, electromagnets may be used to generate an oscillating pulse field gradient (PFG) in between refocusing pulses of Carr Purcell Meiboom Gill (CPMG) pulse sequence. The oscillating PFG may be phase-locked (synchronized) with the CPMG pulses. The pulse field gradient de-phases the spins and then is turned off for a period, during which the spins diffuse. Following the diffusion period, the oscillating pulse field gradient is turned on to re-phase the spins followed by a spin-echo. The first spin-echo is then re-focused by a train of radio frequency 180-degree pulses to obtain more spin-echoes.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Illustrative embodiments of the present disclosure are directed to a nuclear magnetic resonance (NMR) probe. The NMR probe includes a housing with a fluid inlet, a fluid outlet, a longitudinal axis, and an interior volume. The housing contains a fluid sample that is analyzed by the probe. The NMR probe also includes an elongated conductor disposed along the longitudinal axis of the housing. The elongated conductor generates an oscillating electromagnetic field within the interior volume of the housing. The oscillating electromagnetic field produces a NMR signal within the fluid sample. The elongated conductor may also be used to receive this NMR signal. The NMR signal is then analyzed to extract information about the fluid sample.

In more specific embodiments, a power input terminal is electrically coupled to the elongated conductor for providing radio frequency power to the elongated conductor. The radio frequency power generates the oscillating electromagnetic field. Furthermore, a ground terminal is electrically coupled to the housing so that the radio frequency power is localized within the interior volume.

Various embodiments of the present disclosure are also directed to a method for analyzing a composition of a fluid sample. The method includes flowing the fluid sample into a sample volume through a fluid inlet of a coaxial NMR probe. A magnetic field is applied to generate a magnetization within the fluid sample. The magnetic field is applied along a bias magnetization direction. The method also includes applying a pulse sequence to an elongated conductor within the coaxial probe to generate an oscillating magnetic field within the fluid sample. The elongated conductor may be used to receive a magnetic resonance signal from the fluid sample. The received magnetic resonance signal is analyzed to determine information about the fluid sample. The fluid sample flows out of the sample volume through an outlet of the coaxial NMR probe.

Illustrative embodiments of the present disclosure are also directed to another method for analyzing a composition of a fluid sample. The method includes introducing the fluid sample into a sample volume of a coaxial NMR probe. A magnetic field is applied to the fluid sample to generate a magnetization within the fluid sample. The magnetic field is applied along a bias magnetization direction. Also, a composite pulse sequence is applied to an elongated conductor of the coaxial probe to generate an oscillating magnetic field gradient across the fluid sample. The oscillating magnetic field gradient generates a magnetic resonance signal within the fluid sample. The method further includes using the elongated conductor to receive the magnetic resonance signal from the fluid sample. The received magnetic resonance signal can be used to determine information about the fluid sample.

Some embodiments of the present disclosure are directed to a wellbore logging tool. The tool includes an assembly for withdrawing formation fluid from a formation. The tool also includes a flow line for passing the formation fluid through the tool. The flow line is coupled to a NMR probe that analyzes the formation fluid that passes through the flow line. The NMR probe includes a housing with a longitudinal axis and an interior volume. The housing at least partially contains the formation fluid. The probe also includes an elongated conductor that is disposed along the longitudinal axis of the housing. The elongated conductor generates an oscillating electromagnetic field within the interior volume and thus applies the field to the formation fluid.

Illustrative embodiments of the present disclosure are also directed to a coaxial NMR probe that includes a coaxial transmission line. The transmission line includes a central conductor having an outer surface and a metallic shield having an inner surface that surrounds the central conductor. An annular volume between the inner surface and the outer surface defines a sample volume. The annular volume can be used to contain a pressurized fluid sample. The metallic shield serves as a part of a pressure vessel for housing the pressurized fluid sample. A fluid input port allows the pressurized fluid sample to be introduced into the sample volume of the coaxial transmission line. A power input terminal is electrically connected to the central conductor of the coaxial transmission line for providing RF power to the sample volume and a ground terminal is electrically connected to the metallic shield of the coaxial transmission line so that the RF power is localized within the sample volume.

Other aspects and advantages of the disclosure will be apparent from the following description and the appended claims.

BRIEF DESCRIPTION OF DRAWINGS

FIG. 2(A)-(B) show cross sections of a coaxial NMR probe in accordance with one or more embodiments.

FIG. 2(C) shows the magnetic field created by a longitudinal conductor of a coaxial NMR probe in accordance with one or more embodiments.

DETAILED DESCRIPTION

Figure 1:
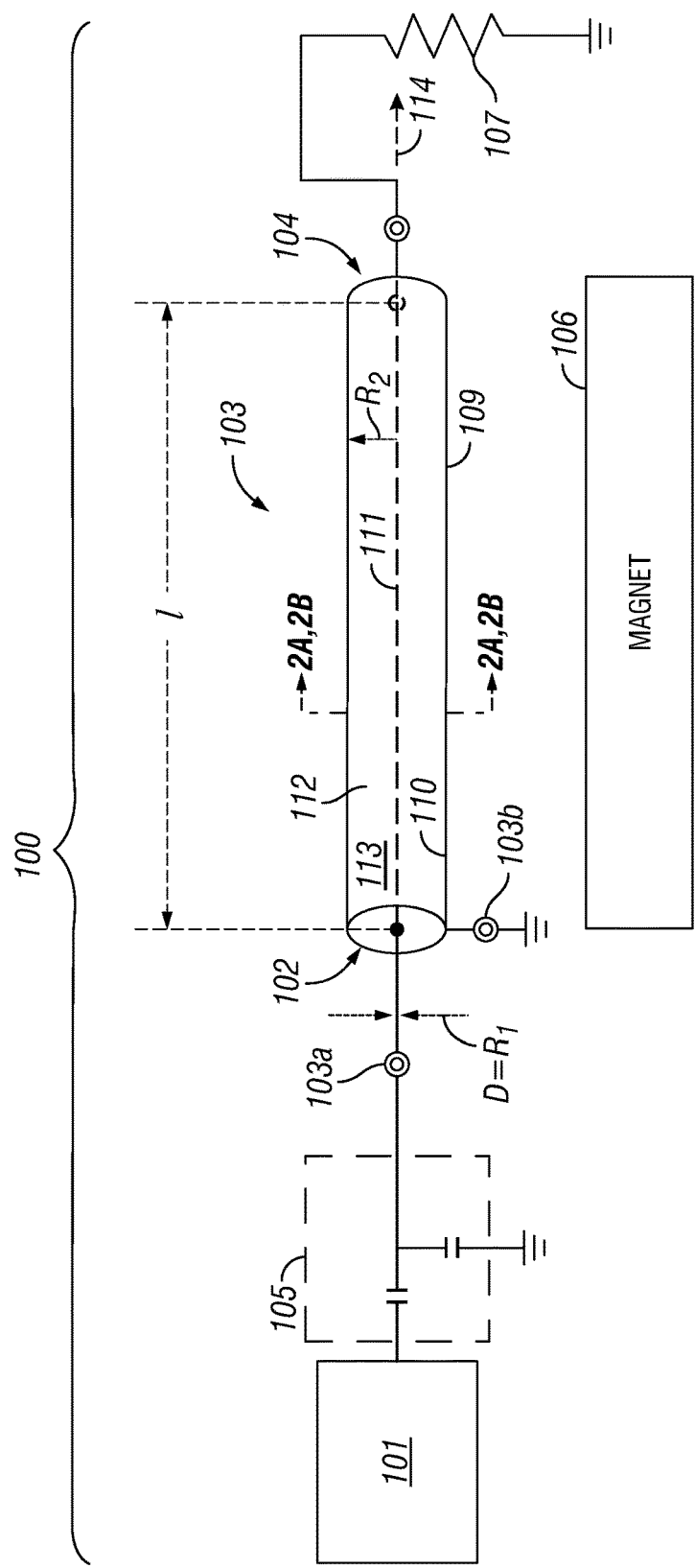
FIG. 1 shows a coaxial NMR probe in accordance with one or more embodiments.

Specific embodiments of an NMR probe and method of use are described in detail with reference to the accompanying figures. Like elements in the various figures (also referred to as FIGS.) are denoted by like reference numerals for consistency.

In the following detailed description of embodiments, numerous specific details are set forth in order to provide a more thorough understanding of the NMR probe and methods of use. However, it will be apparent to one of ordinary skill in the art that these embodiments may be practiced without these specific details. In other instances, well-known features have not been described in detail to avoid unnecessarily complicating the description.

Illustrative embodiments are directed to a coaxial NMR probe for use in an NMR system that may operate in either a laboratory environment or a high-temperature and high-pressure environment. In one embodiment, the probe includes a tubular metallic member with a centrally positioned conductor within the tubular metallic member. The annular interior volume defined by the outer surface of the centrally positioned conductor and inner surface of the tubular metallic member may be filled with a fluid. The centrally positioned conductor is used to generate the oscillating magnetic field used to manipulate the nuclear spins of the fluid (i.e., it may serve as the transmitting antenna) and the centrally positioned conductor may also serve as the sensor for detecting NMR signals emitted from the fluid (i.e., it may serve as the receiving antenna). In other words, the centrally positioned conductor may serve as both the transmitting antenna and the receiving antenna for an NMR system. Furthermore, in accordance with one or more embodiments, the oscillating magnetic field produced in the inner volume also serves as the magnetic field gradient used for spatially encoding the longitudinal magnetization of the spins. Accordingly, one or more embodiments may use the oscillating field gradient as the pulsed gradient for diffusion measurement. Accordingly, in some embodiments, there is no need for a separate pulsed field gradient coil and the associated electronics.

In accordance with one or more embodiments, measurement methods used in conjunction with the NMR probe may obtain valuable NMR properties such as $T_1$, $T_2$ and the diffusion coefficient D, both in a laboratory setting and in a high pressure, high temperature environment, e.g., downhole.

For the sake of simplicity, the examples below will be described in the context of an NMR system that employs an oscillating electromagnetic field having a frequency in the radio frequency (RF) spectrum, e.g., from about 3 kHz to about 300 GHz, and thus the term RF as used herein also encompasses the region of the spectrum commonly referred to in the art as the microwave spectrum, e.g., from about 300 MHz to about 300 GHz. However, it will be appreciated that the precise frequency used depends on both the design of the NMR system (e.g., the value of $B_0$) and the chemical makeup of the fluid under test, and thus any part of the electromagnetic spectrum may be used without departing from the scope of the present disclosure. Thus, in what follows, the term RF should be interpreted broadly and it is understood that other frequencies besides RF may be used in the examples below without departing from the present disclosure. Furthermore, while the examples below are described in the context of NMR measurement, other types of magnetic resonance measurement may be employed without departing from the scope of the present disclosure, e.g., electron spin resonance, electron paramagnetic resonance, or the like.

FIG. 1 shows an NMR system 100 that includes a coaxial NMR probe 103 in accordance with one or more embodiments. The coaxial NMR probe 103 includes an elongated housing 109. The elongated housing includes a fluid inlet 102 and a fluid outlet 104 so that a fluid sample can flow in and out of the housing. In other embodiments, the elongated housing may be an inner surface 110 of a passage that passes through a larger housing block (not shown), in which case, FIG. 1 should be interpreted to show the inner surface of the passage (e.g., as described below in reference to FIG. 5(A)-5(C) below). In addition, in accordance with one or more embodiments, the central conductor 111 may be disposed within the elongated housing 109. The elongated housing 109 includes at least one longitudinal axis 114 and the central conductor 111 is disposed along the longitudinal axis. In various embodiments, the elongated housing 109 and the central conductor 111 are made from conductive materials so that the NMR probe 103 functions as a coaxial transmission line and the elongated housing 109 serves as a shield (or return) of the coaxial transmission line. The elongated conductor 111 is a first electrode of the NMR probe and is configured to generate an oscillating electromagnetic field within the interior cavity of the housing 109. An inner surface of the housing member 109 forms one surface of a pressure vessel that contains the fluid and is also a second electrode of the NMR probe. In accordance with one or more embodiments, the central conductor 111 may disposed centrally within the tube, i.e., it is disposed along a central longitudinal axis 114 of the elongated housing 109. In some embodiments, the elongated central conductor 111 of the coaxial NMR probe is placed off-center without departing from the scope of the present disclosure (e.g., disposed along an off-center longitudinal axis).

As mentioned above, in accordance with one or more embodiments, the tube includes a fluid inlet 102 and a fluid outlet 104 (e.g., one or more ports). The fluid inlet 102 and the fluid outlet 104 may be formed in one or more end caps (not shown) that are coupled to the end of the tube. Furthermore, one or more fluid pumps (not shown) and/or one or more valves (not shown) can be used to provide the fluid sample 113 to the interior cavity 112 of the NMR probe 103. In accordance with one or more embodiments, the fluid sample 113 (e.g., a fluid including water and/or a hydrocarbon) may flow through the fluid inlet 102, and be at least partially contained within the interior cavity 112 of the coaxial NMR probe 103.

The fluid sample 113 may flow from the fluid inlet 102 and to the fluid outlet 104 of the housing 109. In some embodiments, the fluid may also flow in a reverse direction from the fluid outlet 104 to the fluid inlet 102. The present disclosure is not limited to any particular direction of flow within the housing 109 of the probe.

In various embodiments, the NMR measurements and analysis of the fluid sample 113 are performed when the flow of fluid is stopped within the elongated housing 109. To this end, one or more pumps may stop pumping the fluid sample 113 through the housing and/or one or more valves may be closed to stop the flow of fluid through the housing. Stopping the flow of fluid within the housing decreases turbulence of the fluid sample 113 and provides for a more accurate NMR measurement of the fluid sample. In other embodiments, however, the flow of fluid through the housing continues as the NMR measurements are performed. For example, NMR relaxation measurements can be performed while the fluid sample flows through the housing.

As explained further below, by including a fluid inlet and a fluid outlet, the NMR probe can be used to analyze fluid within a flow line. The NMR probe analyzes fluid as it flows through a flow line, such as a tube, a pipe, or a pipeline. In this manner, various embodiments of the NMR probe analyze the fluid in a convenient and time efficient manner without the need for manually charging the probe with fluid. Furthermore, various embodiments of the NMR probe can measure and analyze fluids that are at pressure within the flow line. These characteristics make the NMR probe well suited for oilfield tool applications, where fluids are often at high pressures and manual intervention may not be possible (e.g., wellbore tool applications).

The NMR system 100 also includes an NMR spectrometer 101 that is electrically connected to the coaxial NMR probe 103 by way of terminal 103a. In accordance with one or more embodiments, the NMR spectrometer 101 may be any spectrometer known in the art and thus may include one or more RF transmitters and receivers, as well as one or more RF transceivers, in addition to the various electronics for generating, receiving, synchronizing and storing RF pulses for use in an NMR system. Furthermore, the NMR spectrometer 101 may be configured to provide continuous wave (CW) and/or pulsed RF power to a central conductor 111 of the coaxial NMR probe 103. In accordance with one or more embodiments, an impedance matching network 105 may be used to provide an impedance match between the NMR spectrometer 101 and the coaxial NMR probe 103. In accordance with one or more embodiments, impedance matching may be further improved by terminating the coaxial NMR probe with a resistor 107. A ground terminal 103b electrically couples the housing 109 to ground such that radio frequency power is localized within the interior cavity 112 of the probe.

In accordance with one or more embodiments, the inductance of a coaxial NMR probe may be approximated by:

$$L = \frac{\mu_0 l}{2\pi \ln(r_2/r_1)}$$

where l is the length of the probe, and $r_2$ and $r_1$ are the outer and inner conductor radii, respectively. Thus, for a 1 cm long coaxial NMR probe having a 1 mm diameter outer conductor and a 0.2 mm central conductor, the inductance is approximately 1.2 nH. Accordingly, the tuning capacitor for $f_0$=20 MHz is about 51 nF. While this capacitance is relatively large, the voltage on the capacitors will be small and thus lower specification and much smaller capacitors can be used. For example, to inject 1 A current into a coaxial NMR probe, with the coax impedance of $2\pi f_0 L \sim 0.5$ ohm, 0.5 V RF will be applied.

In accordance with one or more embodiments, the NMR spectrometer 101 may supply RF power to the central conductor 111 of the coaxial NMR probe 103 thereby generating a spatially non-uniform oscillating magnetic field in the interior cavity 112 (e.g., interior volume). In accordance with one or more embodiments, the spatially non-uniform oscillating magnetic field may be used to apply an NMR pulse sequence to the fluid sample 113 while simultaneously encoding spatial information in the sample for diffusion measurements, as described in more detail below in reference to FIGS. 6-13.

FIG. 2(A) and FIG. 2(B) show examples of cross-sections of a coaxial NMR probes in accordance with one or more embodiments. For example, FIGS. 2(A) and 2(B) may be cross-sections of the coaxial NMR probe 103 as shown in FIG. 1. In FIG. 2(A), the central conductor 111a is circular in cross section with a radius of $R_1$. In FIG. 2(B), the central conductor 111b is an elongated planar stripline having an aspect ratio not equal to 1. In both embodiments, the inner radius of the elongated housing members 109a and 109b that surround the central conductors 111a and 111b, respectively, is $R_2$. In accordance with one or more embodiments, the elongated housing members 109a and 109b may be formed from a metallic capillary or metallic tube, and thus, may be adapted for high pressure and high temperature fluid investigations. In these embodiments, the fluid sample 113 will be contained within the annular interior volumes 201a and 201b. In accordance with one or more embodiments, the elongated housing member 109a and 109b may be a pressure vessel, such as a metallic capillary, or may be incorporated into a pressure vessel.

As used herein, the term radial direction is defined as is customary for a cylindrical coordinate system. For example, FIG. 2(C) shows a single current carrying wire and the magnetic field $B_1$ produced with reference to a cylindrical coordinate system. The radial direction is defined by the unit vector $\hat{e}_r$ that points along a radius of the cylinder. The azimuthal direction is defined by a unit vector $\hat{e}_\varphi$ that points in a direction that is tangent to a circle having a center that is located on the z-axis, where the z-axis is defined by the unit vector $\hat{e}_z$ that is collinear with the central longitudinal axis 114 of the cylinder. Thus, in FIG. 2A, an axial current I may flow along the central conductor 111a that is placed along the z-axis, or more generally, a conductor that runs down the center of the elongated housing 109a, and the magnetic field $B_1$ produced by this axial current points substantially in the $\hat{e}_\theta$ direction. Accordingly, for the embodiment shown in FIG. 2A, the contours of constant magnetic field $B_1$ are circular in shape. For the embodiment shown in FIG. 2B, the central conductor 111b is an elongated planar stripline having an aspect ratio not equal to 1. While the current still flows along the central axis 114 of the elongated housing 109b, the magnetic field contours are more elliptical or may be even rectangular, depending on the shape of the stripline central conductor 111b. In some embodiments, the central conductor may be of any shape and be designed to produce magnetic field profiles that are more or less elliptical or rectangular without departing from the scope of the present disclosure.

Using the cylindrical coordinate system described above, and using the circular central conductor shown in FIG. 2A as an example, the magnetic field $\vec{B}_1$ by the electrical current I flowing in the axial, or z-direction, as shown in FIG. 2C, may be written as:

$$\vec{B}_1 = \frac{\mu_0 I}{2\pi r} \hat{e}_\varphi, \quad (1)$$

where $\mu_0$ is the vacuum magnetic permeability and r is the radial distance from the center of the elongated housing member 109a. Accordingly, the magnitude of $\vec{B}_1$ decreases like $1/r$ as the distance r from the central conductor is increased. Stated more precisely then, the change in magnetic field, also referred to herein as the magnetic field gradient $\vec{g}_1$, is along the radial direction and may be expressed as:

$$\vec{g}_1 = -\frac{\mu_0 I}{2\pi r^2} \hat{e}_r. \quad (2)$$

Figure 3A:
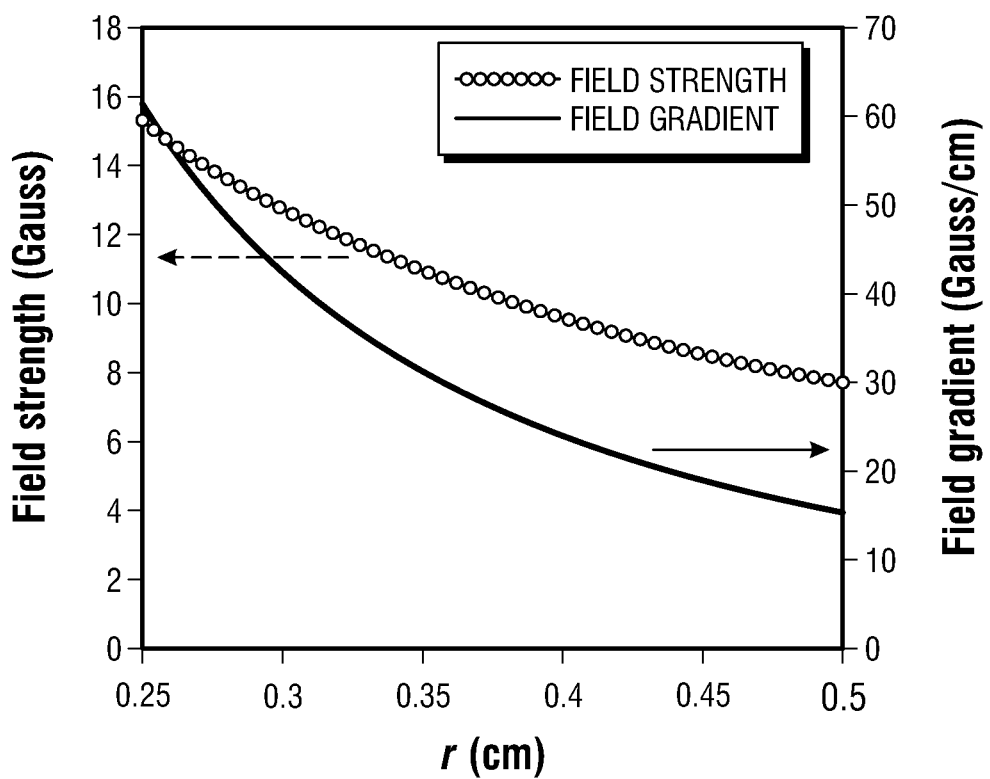
FIG. 3(A) shows $B_1$ and the gradient of $B_1$ within a coaxial NMR probe in accordance with one or more embodiments.
Figure 3B:
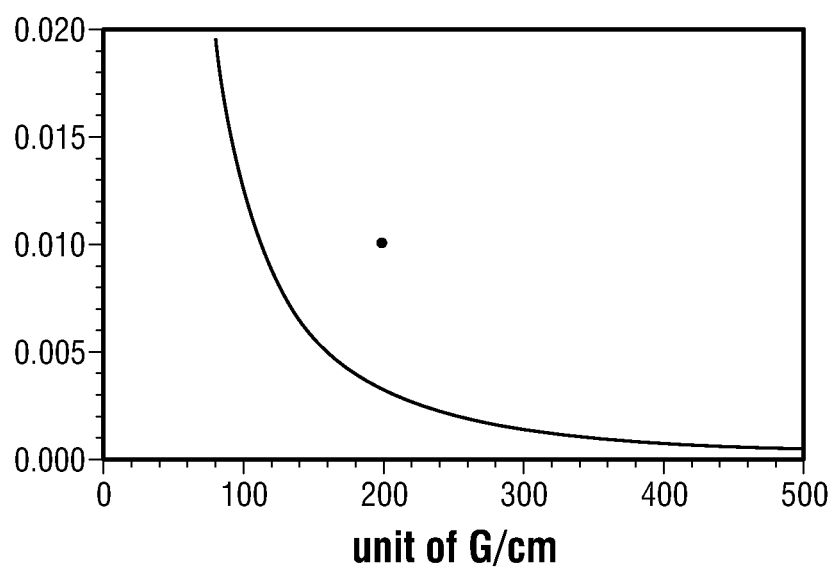
FIG. 3(B) shows a gradient distribution within a coaxial NMR probe in accordance with one or more embodiments.

Thus, in accordance with one or more embodiments of the disclosure, the RF power applied to the probe by an RF source, e.g., a source associated with the NMR spectrometer 101 shown in FIG. 1, will produce an oscillating current I(t) on the central conductor. This oscillating current will, in turn, lead to an oscillating RF magnetic field $B_1(t)$ whose amplitude varies with the radial distance according to Eq. (1) thereby creating a gradient in the RF field amplitude according to Eq. (2). In accordance with one or more embodiments, the RF magnetic field $B_1$ and its gradient $g_1$ both vary considerably as a function of r, as shown in FIG. 3(A). The data shown in FIG. 3(A) correspond to an embodiment of a coaxial NMR probe similar to that shown in FIGS. 4(A)-4(B), where $R_1$=0.50 mm and $R_2$=5.00 mm. FIG. 3(B) shows the gradient distribution for this cylindrical geometry. Accordingly, in various embodiments, the majority of the signal will come from an area with lower gradient adjacent to $r_2$. Nevertheless, the average gradient, shown by the point in FIG. 3(B) is quite substantial.

As shown in FIG. 1, the NMR system 100 also includes a magnet 106 for applying a static magnetic field to interior cavity 112 of the probe 103 that generates a magnetization within the fluid sample. In accordance with one or more embodiments, the magnet 106 and the NMR probe 103 are positioned and configured so that a bias field $B_0$ of the magnet is perpendicular to $B_1$. The time varying field $B_1$ may be used to manipulate the direction of the nuclear spins of the fluid sample and thus perform NMR measurements. Furthermore, due to the geometry, the oscillating field $B_1$ inside the probe also possesses a non-zero radial gradient in amplitude and this radial gradient may be exploited to perform diffusion measurements without the need for a separate set of gradient coils. In other words, the probe exploits the fact that a pulse of the RF field $B_1$ also simultaneously provides a pulsed field gradient $g_1$.

Generally speaking, diffusion measurements using NMR use a separate set of magnetic field coils that are pulsed to spatially encode the spins. However, the added hardware used for this pulsed field gradient (PFG) technique adds substantial cost and complexity to the system. In accordance with one or more embodiments, employing the field gradient in $B_1$ instead of a separately produced gradient field results in a simplified system that is cheaper to manufacture and possesses less stringent space requirements than systems that employ separate gradient coils. Thus, in accordance with one or more embodiments, the coaxial NMR probe may be used in systems were space requirements are tight (e.g., in a down hole NMR logging tool).

In accordance with one or more embodiments, because the oscillating field $B_1$ is along the azimuthal direction, two choices for the bias field $B_0$ are possible, while maintaining $B_1$ and $B_0$ substantially perpendicular to each other, as is beneficial for performing NMR measurements. For example, in accordance with one or more embodiments, the coaxial NMR probe may be placed in a bias magnetic field that is parallel to the long axis (z-axis) of the probe (e.g., as would be the case if the probe was located within the bore of a solenoid magnet). Furthermore, most superconducting magnets are cylindrical in shape and produce a $B_0$ field that lies along the cylinder axis. Thus, as long as the TEM mode of the coaxial probe dominates, one simply has to align the axes of the probe and the magnet for optimal coupling of $B_1$ to the nuclear spins that are magnetized along the $B_0$ direction.

In accordance with one or more embodiments, $B_0$ may be along any direction that is perpendicular to the long axis (z-axis) of the probe, i.e., along a direction that is parallel to a radius of a cylindrical centered on the central conductor. For example, in accordance with one or more embodiments, the magnet 106 is a permanent magnet that is designed as Halbach array, (e.g., a Halbach dipole magnet). This type of magnet is cylindrical in shape and produces a $B_0$ field inside the probe that lies in a plane transverse to the long axis of the probe. In this arrangement, because the direction $B_1$ curls around the central axis of the probe, it may not be possible to keep $B_0$ and $B_1$ perpendicular to each other over the entire sample volume. For example, in a coaxial probe having a central conductor of circular cross-section, the $B_1$ field lines form circular loops, as shown in FIG. 2A, so over roughly half the available sample volume, $B_0$ and $B_1$ may be parallel (or anti-parallel) to each other, resulting in no signal being produced in these regions. This phenomena is illustrated in FIG. 2A where, when installed inside a Halbach magnet, the $B_0$ field will point parallel (or anti-parallel) to the $B_1$ field in regions 203 and 205 and will point perpendicular to the $B_1$ field in the regions 207 and 209.

In accordance with one or more embodiments, the amount of "lost" sample volume can be minimized if the $B_1$ field lines can be distorted from circles into elliptical or rectangular loops, with $B_0$ aligned along the minor axis. In accordance with one or more embodiments, elliptical field lines may be produced by using a flat central conductor within a cylindrical outer conductor, as shown in FIG. 2B. This structure, is referred to herein as a strip-conductor coaxial transmission line. In the case of the strip-conductor coaxial transmission line, most of the signal will be generated from the region 211 directly above and the region 213 directly below the center conductor, where the $B_1$ field lines are approximately parallel to the surface of the flat central conductor.

In accordance with one or more embodiments, the spatial distribution of $B_1$ within the NMR probe should be considered. As discussed above, a coaxial NMR probe generates a non-uniform $B_1$ field within the sample during RF pulses. For example, as described above in reference to Eqs. (1)-(2), in a coaxial probe having a circular central conductor, the magnitude of $B_1$ is inversely proportional to distance r from the center conductor, resulting in a $B_1$ gradient proportional to $1/r^2$. In accordance with one or more embodiments, in a strip-conductor coaxial probe, the $B_1$ gradient decreases approximately linearly with distance from the elongated conductor. While coaxial NMR probes having inner conductors with circular and/or rectangular cross-section are discussed explicitly herein, one of ordinary skill having the benefit of this disclosure will recognize that any shape may be used without departing from the scope of the present disclosure.

Figure 4A:
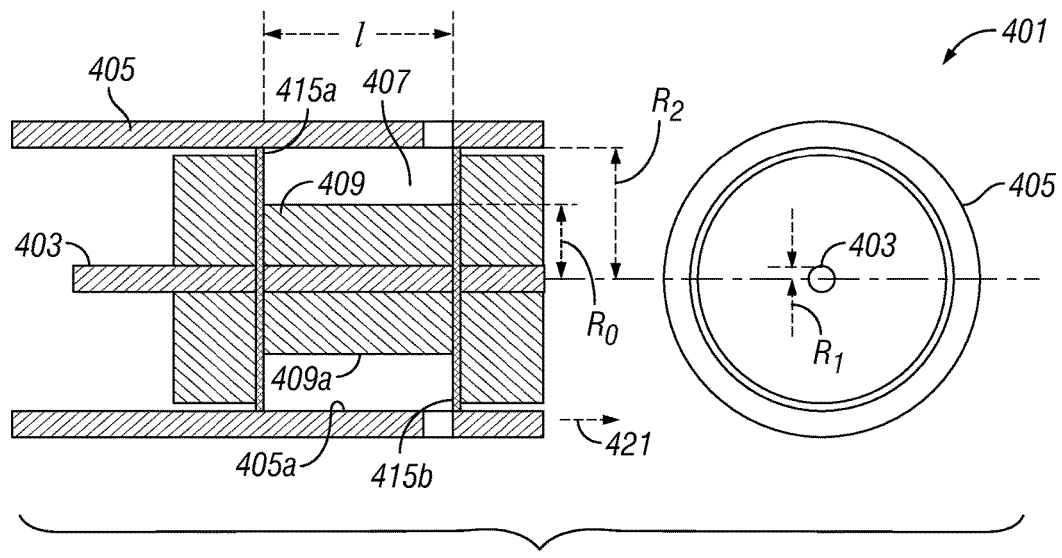
FIGS. 4(A)-4(B) show coaxial NMR probes in accordance with one or more embodiments.
Figure 4B:
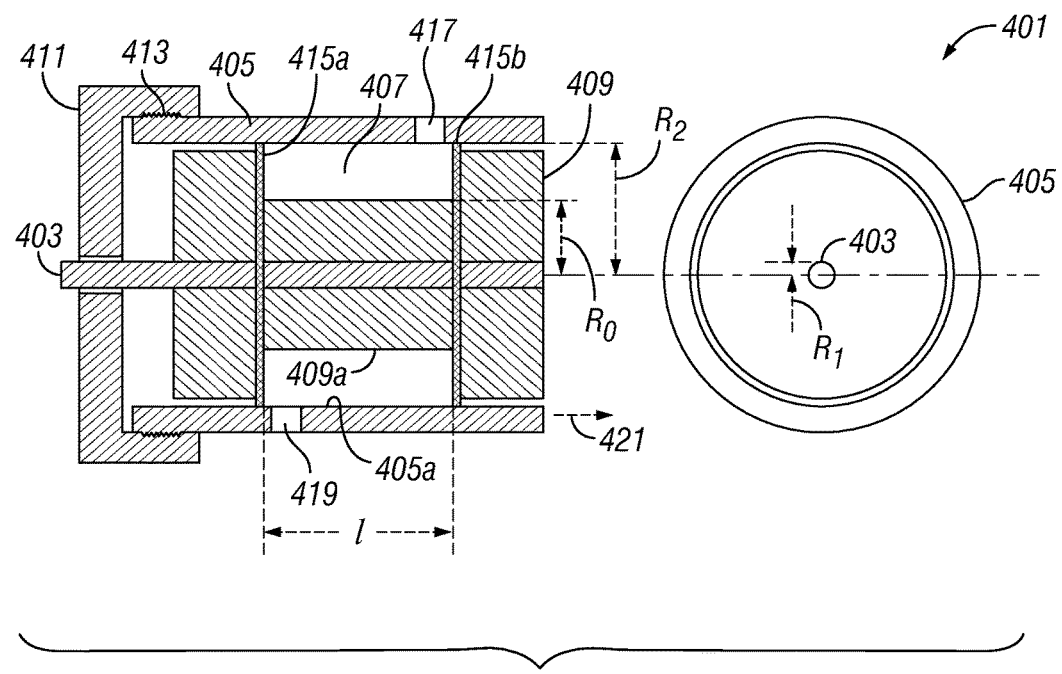

FIGS. 4(A)-4(B) show coaxial NMR probes in accordance with one or more embodiments. Each coaxial NMR probe 401 includes a circular elongated center conductor 403, an outer elongated housing 405, and an annular sample volume 407. The elongated center conductor 403 and outer metallic vessel 405 may be made of high-purity copper (e.g., greater than 99.0% purity), and may be electrically connected at one end to an RF transmitter and receiver (not shown) (e.g., an NMR spectrometer as shown in FIG. 1). The inner central conductor 403 is in the form of a copper wire that is 0.1 cm in diameter ($R_1$=0.05 cm) and the outer elongated housing 405 is 1 cm in inner diameter ($R_2$=0.5 cm). The inner central conductor 403 is fed through an insert 409 (e.g., Teflon™) that insulates the central conductor 403 and also serves as a spacer for the fluid sample that is contained within the annular sample volume 407. The annular sample volume 407 may be located between the outer surface 409a of the insert 409 (e.g., $R_0$=0.25 cm) and the inner surface 405a of the housing member 405 (e.g., $R_2$=0.5 cm). Accordingly, in this embodiment, with a 4 cm housing length (l), the total fluid volume is 2.36 cm$^3$. Of course other fluid volumes are possible without departing from the scope of the present disclosure. The precise dimensions used for this example are not intended to limit the scope of the present disclosure, but rather are disclosed here merely as a specific embodiment. For example, in some embodiments, the inner elongated central conductor 403 can have a diameter of 0.1 mm to 5 mm and the outer elongated housing 405 can have a diameter of 1 mm to 5 cm. Also, housing length (l) can be between 2 mm and 10 cm (e.g., housing length is also represented by l in FIG. 1).

In accordance with one or more embodiments, the coaxial NMR probe 401 may be connected to an electronic tuning circuit to ensure frequency tuning and impedance matching, as shown in FIG. 1.

FIG. 4(A) shows an open geometry and FIG. 4(B) shows a closed geometry. In the closed geometry, an end cap 411 may be threaded onto one end of the elongated housing 407 by way of threaded connection 413. In accordance with one or more embodiments, the end cap 411 is electrically isolated from the central conductor 403 (e.g., by way of a bushing or an external coating to the central conductor 403). In both embodiments shown in FIGS. 4(A) and 4(B), O-ring seals 415a and 415b may seal the annular sample volume from the remainder of the probe's internal volume. In accordance with one or more embodiments, the open geometry embodiment shown in FIG. 4(A) may be charged with fluid manually. The closed geometry embodiment shown in FIG. 4(B) may be charged with fluid using a fluid inlet 417 that extends through the housing 405. The fluid may then exit the sample volume 407 using a fluid outlet 419 that also extends through the housing 405. In further embodiments, the fluid inlet 417 and/or fluid outlet 419 are disposed in other locations. For example, the fluid inlet 417 and/or fluid outlet 419 may extend through the end cap 411 and the insert 409 of the probe.

FIGS. 4(A)-4(B) show a partial view of the coaxial NMR probes. The central conductor 403, the outer elongated housing 405, and the insert 409 may extend further in the direction of arrows 421. In this manner, the probes form coaxial transmission lines.

Figure 5A:
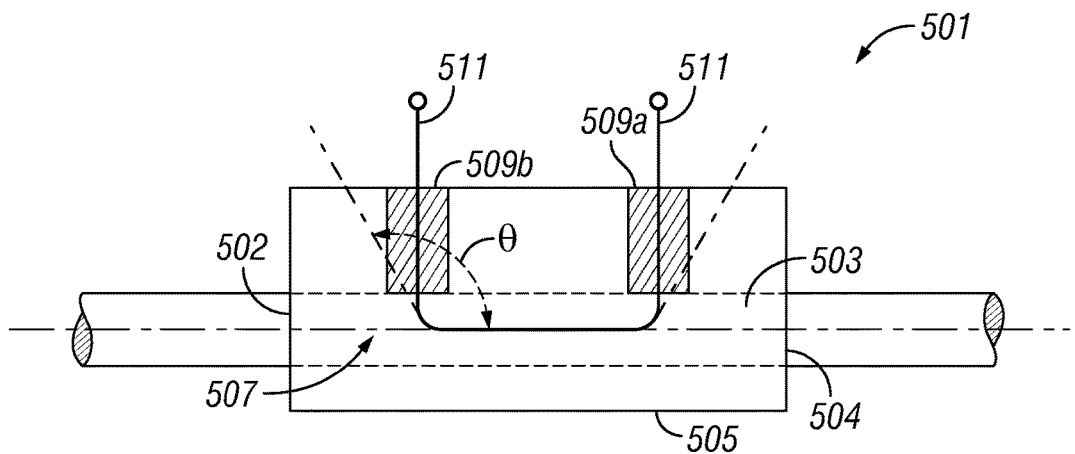
FIG. 5(A)-5(C) show coaxial NMR probes in accordance with one or more embodiments.

In accordance with one or more embodiments, the geometry of the coaxial NMR probe may facilitate implementation within a wellbore tool flow line and/or a metallic pressure vessel or housing for handling high pressures in wellbore conditions (e.g., 30,000 psi). For example, FIG. 5A shows a coaxial NMR probe 501 implemented within a flow line 503 in accordance with one or more embodiments. While this example is described here in the context of a wellbore tool flow line, the various NMR probe embodiments disclosed herein may be adapted to be employed within a stand-alone laboratory instrument or within a wellbore tool without departing from the scope of the present disclosure. In this embodiment, the flow line 503 is coupled to and passes through a metal block 505 that forms the elongated housing of coaxial NMR probe. In particular, the flow line 503 passes through a fluid inlet 502 and a fluid outlet 504 of the metal block. The fluid may also flow in the opposite direction. In accordance with one or more embodiments, the metal block 505 may be made of titanium and the elongated housing is formed from a cylindrical passage 507 bored through the length of the metal block 505. Two feed-throughs 509a and 509b allow an elongated central conductor 511 to pass through the metal block 505 and into the elongated housing formed by cylindrical passage 507. In accordance with one or more embodiments, the feed-throughs 509a and 509b may enter at an obtuse angle θ to facilitate assembly. Furthermore, in accordance with one or more embodiments, the fluid inlet 502 and fluid outlet 504, respectively, may not be disposed opposite from each other, as shown in FIG. 5A. Other configurations are also possible without departing from the scope of the present disclosure. For example, the fluid inlet 502 and fluid outlet 504 may be disposed on the same side of the block 505 or the fluid inlet 502 and fluid outlet 504 may be disposed perpendicular to each other.

In accordance with one or more embodiments, the coaxial NMR probe 501 may be placed into and/or adjacent to an NMR magnet, such as a Halbach array or the like. Also, in some embodiments, a flat inner conductor like that described above in reference to FIG. 3B may be disposed inside the cylindrical passage 507 to increase the internal volume where $B_1$ is perpendicular to $B_0$ and thereby also increase the NMR signal.

Figure 5B:
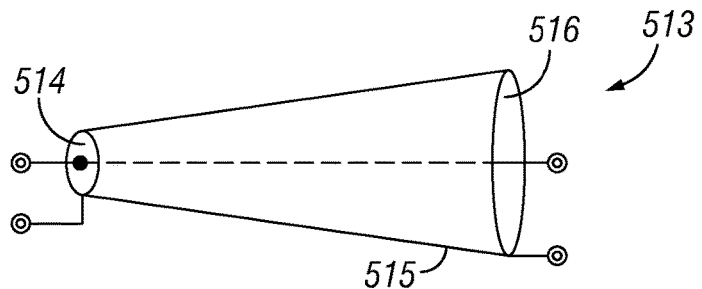
Figure 5C:
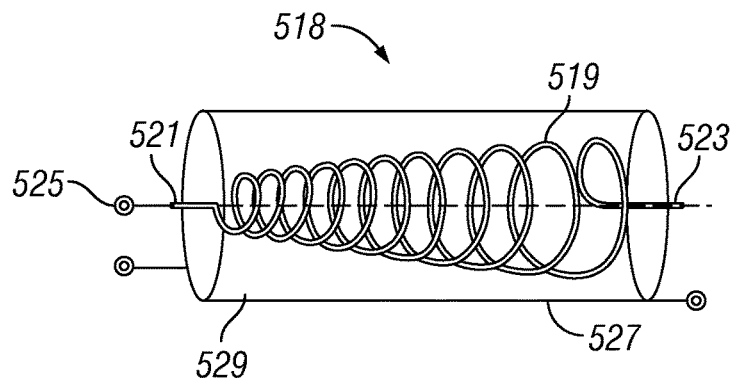

FIG. 5(B) shows a coaxial NMR probe 513 implemented within a flow line 515 in accordance with one or more embodiments. In this embodiment, the flow line 515 includes a fluid inlet 514 and a fluid outlet 516. The flow line 515 is shaped as a truncated cone where the radial motion of molecules may be detected by the $B_1$ field gradient. FIG. 5(C) shows another embodiment of the coaxial NMR probe 518 that includes a fluid channel 519 that is shaped as a conical helix. The fluid channel 519 includes a fluid inlet 521 and a fluid outlet 523. The fluid channel 519 is disposed within an elongated housing 527 and the channel turns around a central conductor 525. The volume 529 between the fluid channel 519 and the elongated housing 527 may be filled with a fluid that is unresponsive to NMR, such as air, fluorinated oil, or deuterated fluid. In FIGS. 5(B) and 5(C), the fluid sample may flow from the inlet to the outlet or, in the reverse direction, from the outlet to the inlet. In some embodiments, the flow rate of the fluid sample may be detected using the structures shown in FIGS. 5(B) and 5(C). The radial displacement of protons in the fluid may be detected as the fluid flows along the length of the probe.

Figure 6:
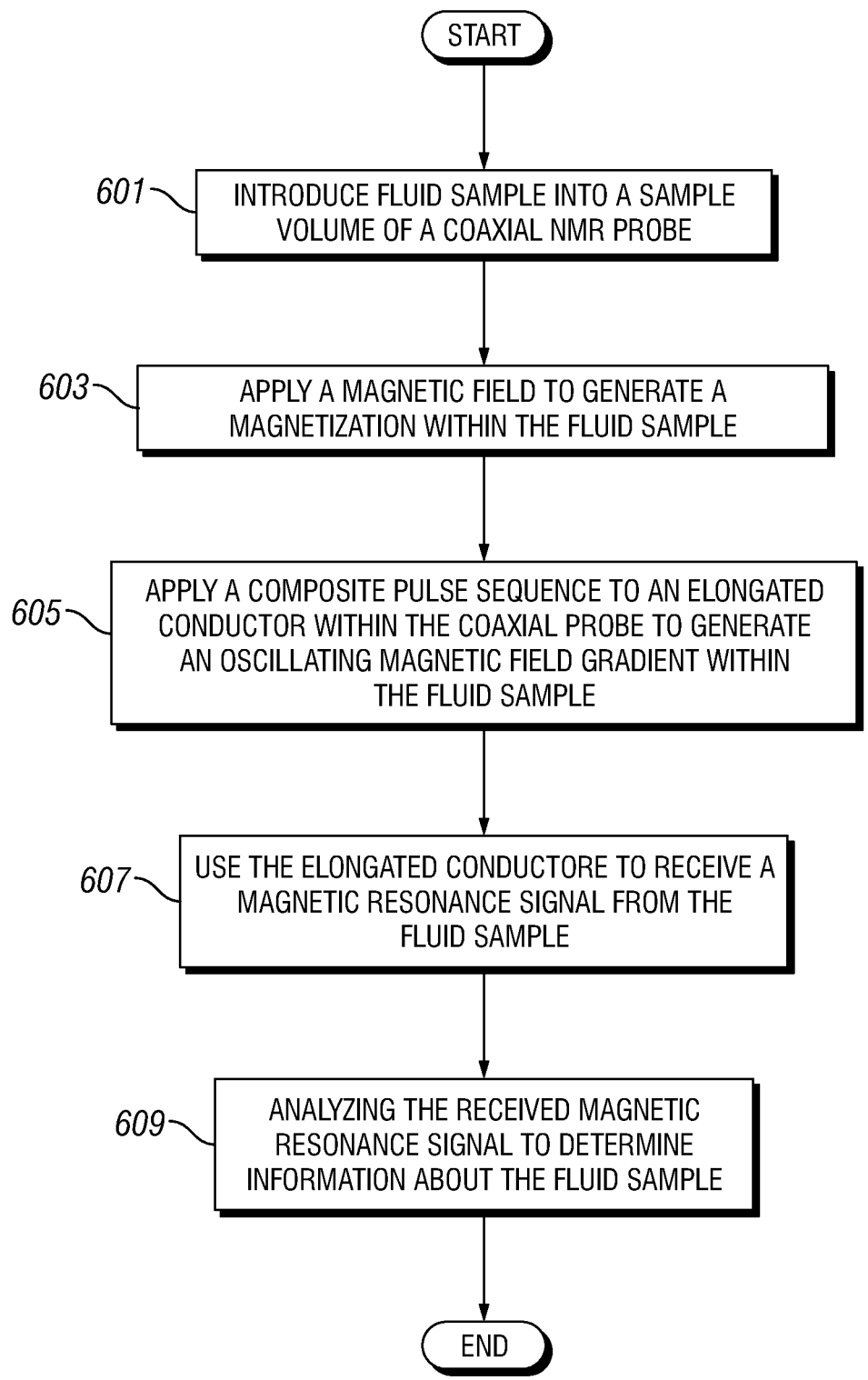
FIG. 6 shows flow chart that illustrates a method in accordance with one or more embodiments.

FIG. 6 is a flow chart illustrating a method of conducting an NMR measurement using a coaxial NMR probe in accordance with one or more embodiments. In process 601, fluid is introduced into an annular sample volume of a coaxial NMR probe. For example, the probe may be of the type described above in reference to FIGS. 1-2, and 4-5. Accordingly, the annular sample volume may be defined by an inner surface of a metallic shield or flow line of the coaxial NMR probe and an outer surface of a central conductor of the coaxial NMR probe. Furthermore, in accordance with one or more embodiments, the fluid may be provided in a flow through configuration or may be statically contained within the coaxial NMR probe.

In process 603, a magnetic bias field is applied to generate a longitudinal magnetization of the fluid sample. For example, bias magnetization $B_0$ may be along any direction that is perpendicular to the long axis (z-axis) of the probe, i.e., along a direction that is parallel to a radius of a cylindrical centered on the central conductor. Accordingly, in accordance with one or more embodiments, permanent magnets designed as Halbach arrays may be used, e.g., a Halbach dipole magnet. Other magnets may be used, e.g., a solenoid or permanent magnet configuration that provides a $B_0$ that is parallel to the long axis of the probe.

In process 605, an oscillating transverse magnetization of the fluid sample is generated by pulsing an oscillating magnetic field $B_1$ in the annular sample volume. For example, the oscillating magnetic field $B_1$ may be provided by applying one or more pulses of RF power to an elongated central conductor of the coaxial NMR probe shown in FIGS. 1-2 and 4-5. The details of the numerous types of pulse sequences that may be used are set forth below in further detail in reference to FIGS. 7-13.

In process 607, a magnetic resonance signal from the fluid is received by the elongated central conductor of the coaxial probe. As described below, this signal may be related to a free induction decay, a spin echo, or a rotary echo in accordance with one or more embodiments. Other magnetic resonance signals may be received without departing from the scope of the present disclosure.

In process 609, the received magnetic resonance signals are analyzed to extract information about the fluid under test. In accordance with one or more embodiments, the signals may be used to determine the relaxation times $T_1$, $T_2$, and/or the diffusion constant D of the fluid under test.

In accordance with one or more embodiments, the analysis of the received magnetic resonance signals may be done on any type of computing device known in the art (e.g., a computer processor). Furthermore, in accordance with one or more embodiments, the analysis may include numerical fitting routines, numerical inversion routines, or the like. The details of the numerical procedures used to extract $T_1$, $T_2$, and/or the diffusion constant D are discussed in more detail below in reference to FIGS. 7-13.

As described above, in accordance with one or more embodiments, a coaxial NMR probe employs a $B_1$ field that varies appreciably within the fluid sample and may be used for diffusion encoding. Furthermore, the elongated housing may be adapted to withstand high pressure, making the probe compatible for fluid analysis downhole. In accordance with one or more embodiments, the coaxial NMR probe may be used to determine fluid properties, such as the relaxation times $T_1$ and $T_2$ and may also be used to determine the fluid diffusion coefficient D. In accordance with one or more embodiments, the coaxial NMR probe may be used to obtain two-dimensional $T_1$-$T_2$ and D-$T_2$ maps for fluid typing as described in more detail below.

Due to the intrinsic $B_1$ inhomogeneity within the coaxial NMR probe, an ideal π/2 pulse that flips spins by 90 degrees (a so-called π/2 pulse) and/or 180 degrees (a so-called π pulse) does not exist. Accordingly, nominal π/2 and nominal π pulses may be defined as RF pulses that have a duration $\tau_{90}$ and $\tau_{180}$, respectively. In accordance with one or more embodiments, the nominal π/2 pulse may render the maximum transverse magnetization over the whole sample and the duration of the nominal π pulse may be defined as twice the duration of the nominal π/2 pulse. In a related manner, the duration of the nominal π/2 pulse may be defined according to the relation:

$$\gamma \langle B_1 \rangle \tau_{90} = \frac{\pi}{2}, \quad (3)$$

where $\langle B_1 \rangle$ represents the spatial average of the amplitude of the $B_1$ field within the coaxial NMR probe and $\gamma$ is the gyromagnetic ratio of the spin being manipulated.

In accordance with one or more embodiments, $\tau_{90}$ may be determined in practice by measuring (or computing based on the known probe geometry) the spatial distribution of $B_1$, computing the average field, and then using Eq. (3). In addition, in accordance with one or more embodiments, $\tau_{90}$ may be determined experimentally by determining the pulse duration that results in the maximum transverse magnetization over the whole sample.

Figure 7:
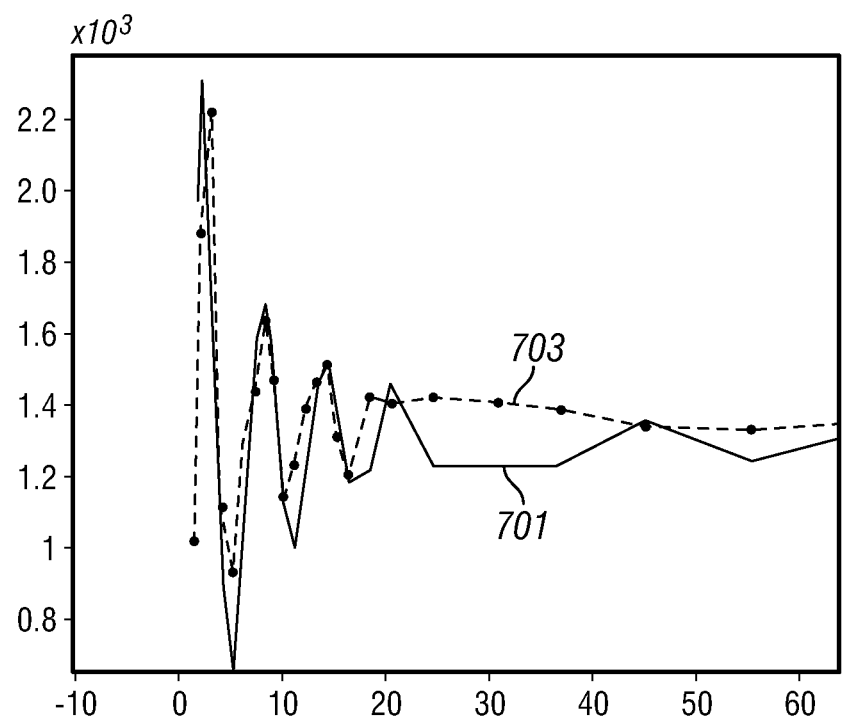
FIG. 7 shows measured spin echo strength as a function of second pulse length for determining a nominal $\pi/2$ pulse in accordance with one or more embodiments.

The experimental determination of $\tau_{90}$ according to Eq. (3) above may be accomplished as follows. In accordance with one or more embodiments, a two pulse experimental sequence may be employed. For each run, the first pulse is fixed (e.g., at length $t_p$=7 μs) while the second pulse of duration t varies. In this experiment, the echo strength measured after the pulse sequence may be written as:

$$SE(t_p, t) = \int_{b_1}^{b_2} \frac{\sin(B_1 \gamma t_p)(1 - \cos(B_1 \gamma t))}{2B_1^2} dB_1, \quad (4)$$

where $b_2$ and $b_1$ are the $B_1$ strengths at a fluid volume furthest from the elongated central conductor and at a fluid volume closest to the central conductor of the NMR probe, respectively. FIG. 7 shows a fit 701 to the data 703 obtained using the coaxial NMR probe shown in FIG. 5(A) and using Eq. (4). From the fit, $b_1$ and $b_2$ are determined and the magnetic field and gradient strength were subsequently determined based on the known geometry of the system. It should be noted that the above method assumes that the interpulse spacing is much shorter than $T_2$ and that diffusion effects may be ignored. By this method, it was determined that $B_1$ varied from 15.3 G to 7.65 G, and the field gradient $g_1$ ranged from 61.2 G/cm to 15.3 G/cm, as shown previously in FIG. 3(A). Correspondingly, by Eqn. (3), the duration $\tau_{90}$ of the nominal π/2 pulse was 5.35 μs and the duration $\tau_{180}$ of the nominal π pulse was 10.7 μs.

In accordance with one or more embodiments, any type of pulse sequences may be used in conjunction with the coaxial NMR probe without departing from the scope of the present disclosure. For example, FIGS. 8-13 show pulse sequences that may be used to make relaxation and diffusion measurements of an unknown fluid sample in accordance with one or more embodiments. Other sequences may be used without departing from the scope of the present disclosure.

Figure 8A:
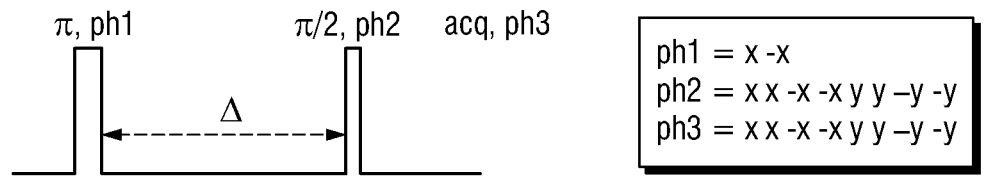
FIG. 8(A) shows an inversion recovery pulse sequence in accordance with one or more embodiments.

FIG. 8(A) shows an inversion recovery pulse sequence for measuring $T_1$ in accordance with one or more embodiments of the present disclosure. As shown in FIG. 8(A), a single inversion recovery pulse sequence includes a nominal π pulse of duration $\tau_{180}$ followed by a delay of duration Δ and followed by a nominal π/2 pulse of duration $\tau_{90}$. The free induction decay (FID) signal is then measured immediately, or shortly after, the nominal π/2 pulse, indicated by "acq" in FIG. 8(A). In accordance with one or more embodiments, a $T_1$ measurement procedure includes a set of inversion recovery pulse sequences, each having a different delay Δ, e.g., using a logarithmic time grid for the set of Δ's. Thus, in accordance with one or more embodiments, a $T_1$ measurement may include a set of FID measurements using the pulse sequences described above. The phase cycling schemes are shown in FIG. 8(A) is designed to select the desired inversion-recovery signal. Other phase cycling schemes may be used without departing from the scope of the present disclosure.

In accordance with one or more embodiments, the response of the coaxial probe to the inversion recovery sequence of FIG. 8(A) is given by:

$$M_{T_1}(\Delta) = M_0 \int_{\omega_-}^{\omega_+} d\omega_1 \frac{\sin(\omega_1 \tau_{90})}{\omega_1^2} [1 + [\cos(\omega_1 \tau_{180}) - 1]e^{-\Delta/T_1}] \quad (5)$$

where $M_0$ is the initial amplitude of the FID signal, $\omega_1$ is the local spin nutation frequency, which is a function of position from the elongated central conductor of the NMR probe, and $\omega_+$ and $\omega_-$ are the local spin nutation frequencies at a fluid volume furthest from the elongated central conductor ($\omega_+ = \gamma b_2$) and at a fluid volume closest to the central conductor ($\omega_- = \gamma b_1$), respectively.

In accordance with one or more embodiments, an alternate form of the response may be used that is based on the difference signal $\delta M(\Delta) = M_{T_1}(\Delta \to \infty) - M_{T_1}(\Delta)$:

$$\delta M_{T_1}(\Delta) = \quad (6)$$
$$M_0 \int_{\omega_-}^{\omega_+} d\omega_1 \frac{\sin(\omega_1 \tau_{90})}{\omega_1^2} [\cos(\omega_1 \tau_{180}) - 1]e^{-\Delta/T_1} = M_0 B e^{-\Delta/T_1}.$$

Eq. (6) shows that, using the difference signal, the $T_1$ kernel has the exponential form:

$$k_{T_1}(\Delta) = Be^{-\frac{\Delta}{T_1}}, \quad (7)$$

where the calibration constant B is given by:

$$B = \int_{\omega_-}^{\omega_+} d\omega_1 \frac{\sin(\omega_1 \tau_{90})}{\omega_1^2} [\cos(\omega_1 \tau_{180}) - 1]. \quad (8)$$

In accordance with one or more embodiments, many fluids of interest have complex compositions and their response in the coaxial NMR probe cannot be described by a single $T_1$ relaxation time. In such cases, the one dimensional distribution function $f(T_1)$ may adequately capture the relaxation behavior resulting in the following form for the difference signal:

$$\delta M_{T_1}(\Delta) = \int dT_1 f(T_1) k_{T_1}(\Delta). \quad (9)$$

In accordance with one or more embodiments, the distribution function $f(T_1)$ may be recovered from the data using Laplace inversion or a multi-exponential fit to the data.

Likewise, $T_1$ for a single component fluid may be extracted from a single exponential fit to the acquired data.

Figure 8B:
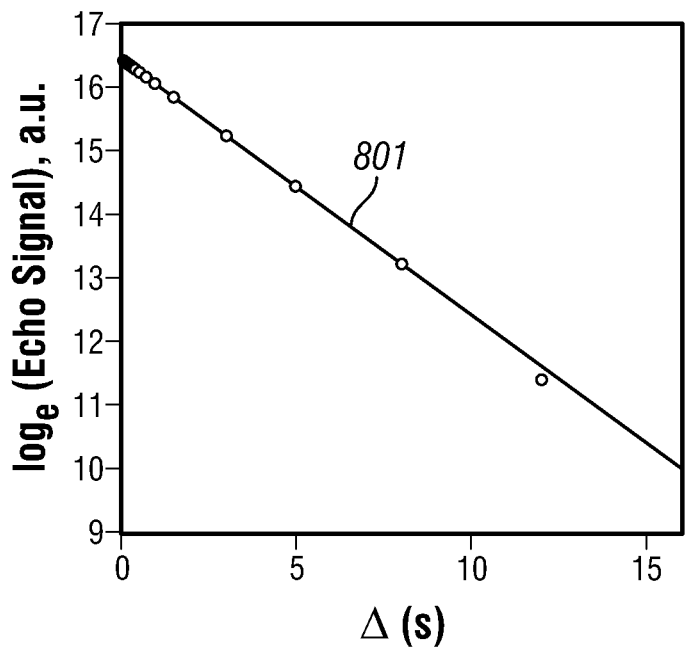
FIGS. 8(B)-8(C) show inversion recovery data acquired using a coaxial NMR probe in accordance with one or more embodiments.

FIG. 8(B) shows data acquired using the coaxial NMR probe of FIG. 5 filled with water. A set of inversion recovery sequences shown FIG. 8(A) were used with a nominal π/2 pulse duration $\tau_{90}$ of 5.35 μs and a nominal π pulse duration $\tau_{180}$ of 10.7 μs. The set of sequences is formed by varying Δ from 0 to 16 s in a logarithmically spaced interval. FIDs for each sequence of the set were recorded immediately after the π/2 pulse. The FID amplitude at Δ=16 s is subtracted from data points to obtain a difference signal, as expressed in Eq. (6) above. The solid line 801 shows a single exponential decay fit to the difference signal.

Figure 8C:
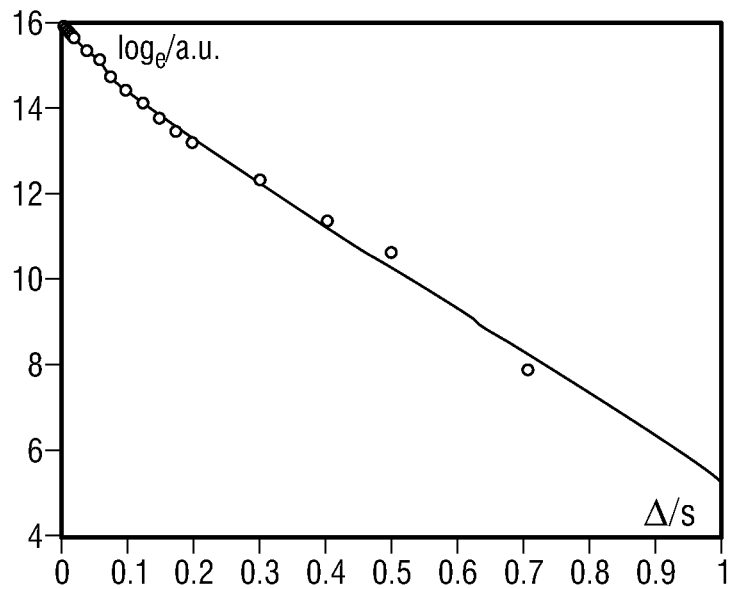

FIG. 8(C) shows data acquired using the coaxial NMR probe of FIG. 5 filled with mineral oil (CVS mineral oil usp), which is a mixture of alkanes with carbon number ranging from 15 to 40. Single exponentials do not fit the $T_1$ data. FIG. 8(C) shows a double-exponential-fit 803 where $T_1$ of the two components are determined to be 40 ms and 100 ms, one order of magnitude shorter than that of water. Likewise, a Laplace inversion algorithm may be applied to extract a continuous distribution of $T_1$.

Figure 9A:
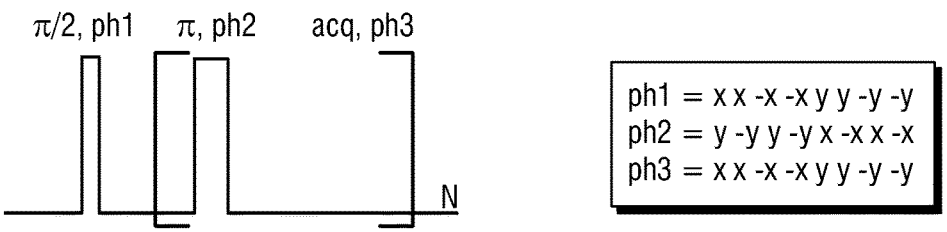
FIG. 9(A) shows a spin echo pulse sequence in accordance with one or more embodiments.

FIG. 9(A) shows a Carr-Purcell-Meiboom-Gill (CPMG) pulse sequence that may be used to measure $T_2$ in accordance with one or more embodiments. In accordance with one or more embodiments, the CPMG pulse sequence is used to induce and measure a spin echo decay signal. The sequence begins with a nominal π/2 pulse of duration $\tau_{90}$ flowed by a series of nominal π pulses each having a duration $\tau_{180}$ to induce the refocusing of the spins for production of the spin echoes. In one embodiment, the nominal π pulses are separated by a time delay of duration $t_E$. In other embodiments, the duration may vary for each pulse depending on the design of the experiment. In accordance with one or more embodiments, a spin echo signal is acquired by the coaxial NMR probe after each nominal π pulse of duration $\tau_{180}$. This is indicated in FIG. 9(A) by "acq." Due to the wide distribution of RF field strength, and thus wide distribution of local spin nutation frequency ($\omega_1 = \gamma B_1$) within the sample volume, the amplitudes of the first few CPMG echoes show large fluctuations that quickly average out before the echo amplitudes approach an asymptotic regime. The echo amplitudes in the asymptotic regime are given by $$M_{T_2,asy}(nt_E) = M_0 \int d\omega_1 f(\omega_1)\omega_1 \sin(\omega_1 \tau_{90}) e^{-\frac{nt_E}{T_{2,eff}}}, \quad (10)$$

where $f(\omega_1)$ is the distribution function for $\omega_1$ that for the coaxial NMR probe geometry in FIG. 3(A) is $f(\omega_1)=1/\omega_1^3$, $t_E$ is the echo spacing, n is the echo number, and $T_{2,eff}$ is the measured spin-spin relaxation time. The measured relaxation time $T_{2,eff}$ includes two contributions due to the intrinsic spin-spin relaxation time $T_2$ and due to the diffusion of the spins in the RF gradient $T_{2,diff}$.

$$\frac{1}{T_{2,eff}} = \frac{1}{T_2} + \frac{1}{T_{2,diff}}. \quad (11)$$

The RF gradient induces a spatial modulation of the magnetization within the sample volume. In the limit of negligible $B_0$ inhomogeneity, the modulation is characterized by the local wave vector:

$$q(r)=\gamma g_1(r)\tau_{90}. \quad (12)$$

Diffusion of the spins within the fluid causes an attenuation of the spin echo signal having a decay rate of:

$$\frac{1}{T_{2,diff}} = q^2 D. \quad (13)$$

Accordingly, the diffusion induced decay rate can be rewritten as:

$$\frac{1}{T_{2,diff}} = \frac{D\pi^2}{2r_{ave}^2}, \quad (14)$$

where $r_{ave}$ is related to the average sample radius. Thus, to the first order, the diffusive contribution does not depend on the echo spacing. Furthermore, for a coaxial probe geometry with a typical size of a fraction of a centimeter, the above analysis shows that the diffusion term is negligible even for fluids having a diffusion coefficient as high as [$10^{-7}$ m²/s]. Thus, in accordance with one or more embodiments, $T_{2eff}$ is approximately equal to $T_2$. This shows that the kernel for the $T_2$ measurement in the asymptotic limit is well approximated by the exponential form:

$$k_{T_2}(nt_E) = Ae^{-\frac{nt_E}{T_2}}, \quad (15)$$

where:

$$A = \int_{\omega_-}^{\omega_+} d\omega_1 \frac{\sin(\omega_1 \tau_{90})}{\omega_1^2}. \quad (16)$$

is the calibration constant.

In accordance with one or more embodiments, many fluids of interest have complex compositions and their response in the coaxial NMR probe cannot be described by a single $T_2$ relaxation time. In such cases, a one dimensional distribution function $f(T_2)$ may adequately capture the relaxation behavior resulting in the following form for the difference signal:

$$M_{T_2,asy}(nt_E)=\int dT_2 f(T_2)k_{T_2}(nt_E). \quad (17)$$

In accordance with one or more embodiments, the distribution function $f(T_2)$ may be recovered from signal data using Laplace inversion or a multi-exponential fit. Likewise, $T_2$ for a single component fluid may be extracted from a single exponential fit.

Figure 9B:
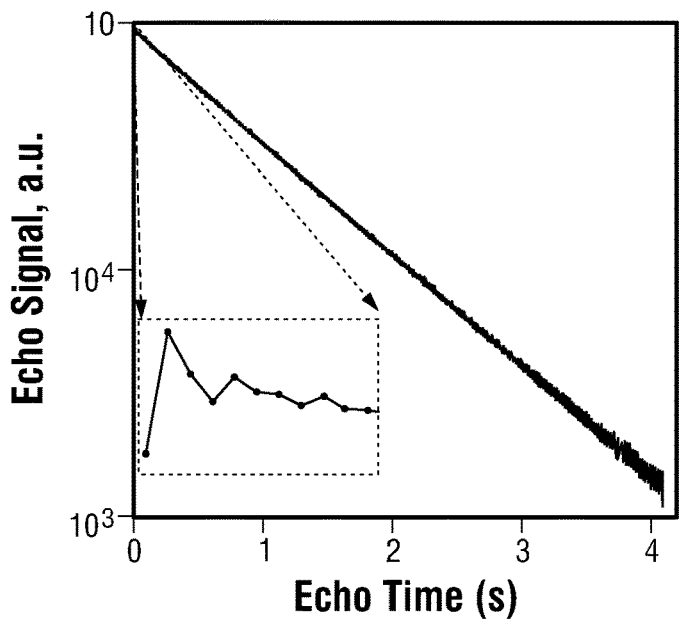
FIG. 9(B)-9(C) show spin echo data acquired using a coaxial NMR probe in accordance with one or more embodiments.

FIG. 9(B) shows data acquired using the coaxial NMR probe of FIG. 5 filled with water and using the set of CPMG pulse sequences of FIG. 9(A) with a nominal π/2 pulse duration $\tau_{90}$ of 5.35 μs, a nominal π pulse duration $r_{180}$ of 10.7 μs, and an echo spacing $t_E$ of 4 ms. For each sequence, a total of 1024 echoes were recorded and to an exponential decay. Form this data $T_2$ is determined to be 1.93 s. The difference between the measured $T_2$ and the measured $T_1$ is likely due to an oxygen affect. For this measurement, the interpulse spacing is much shorter than $T_2$ and diffusion effects have been ignored. The inset of FIG. 9(B) shows the transient effect in the initial few echoes before the asymptotic regime is reached, as alluded to above. As noted above, this effect is due to the inhomogeneity of the $B_1$ field in the coaxial NMR probe.

Figure 9C:
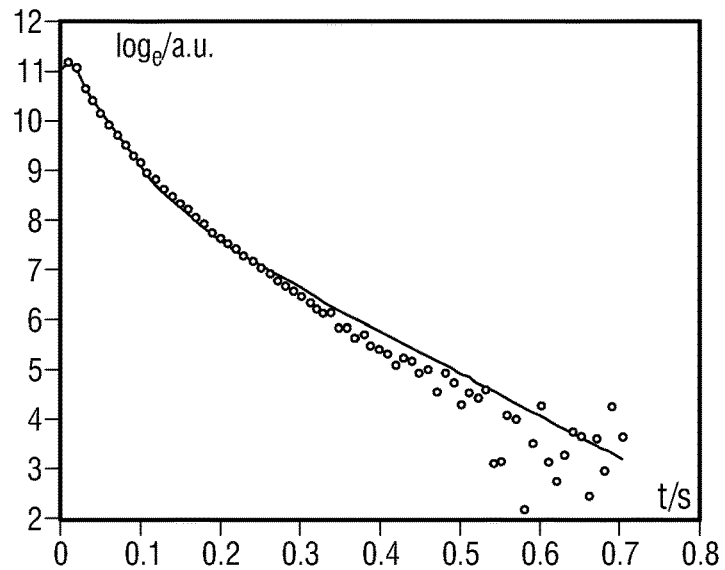

FIG. 9(C) shows data acquired using the coaxial NMR probe of FIG. 5 filled with mineral oil (CVS mineral oil usp), which is a mixture of alkanes with carbon number ranging from 15 to 40. Single exponentials do not fit the $T_2$ data. FIG. 9(C) shows a double-exponential-fit where $T_2$ of the two components is determined to be 37 ms and 110 ms.

Figure 10A:
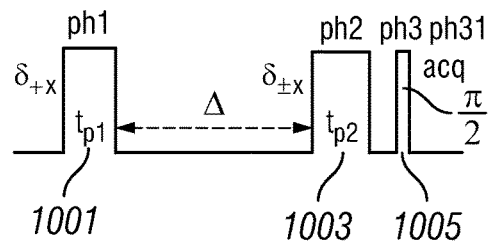
FIG. 10(A) shows a rotary echo pulse sequence in accordance with one or more embodiments.
Figure 10B:
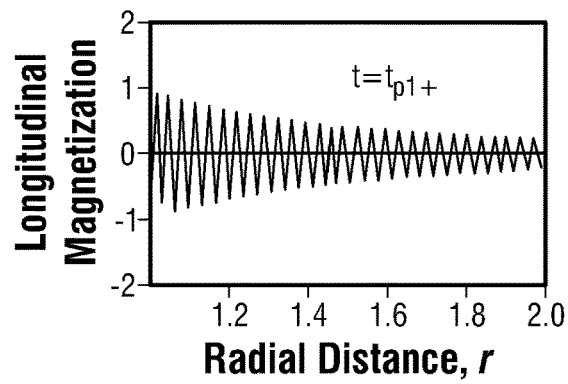
FIGS. 10(B)-10(D) show diagrams of the modulation of the longitudinal magnetization generated by applying the rotary echo pulse sequence in accordance with one or more embodiments.

FIG. 10(A) shows a stimulated rotary-echo pulse sequence used to make diffusion measurements in accordance with one or more embodiments. A rotary echo pulse sequence begins with a winding pulse of duration $t_{p1}$ that spatially modulates the longitudinal magnetization of the spins in the radial direction, as shown in FIG. 10(B). In accordance with one or more embodiments, the spatial modulation is described by the wavenumber q (similar to Eq. 12, above):

$$q(r) = \gamma g_1(r) t_p = \frac{2\pi}{\gamma \mu_0 I} \omega_1^2 t_p. \qquad (18)$$

Figure 10C:
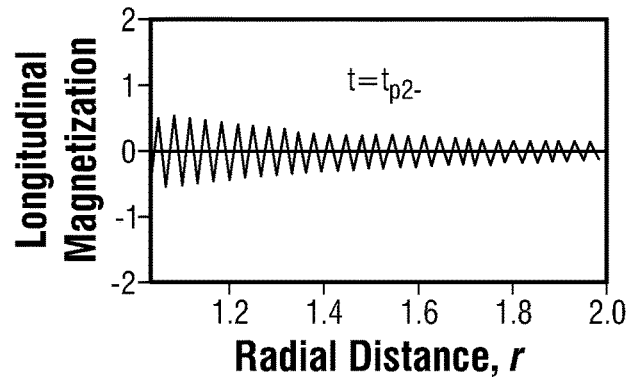
Figure 10D:
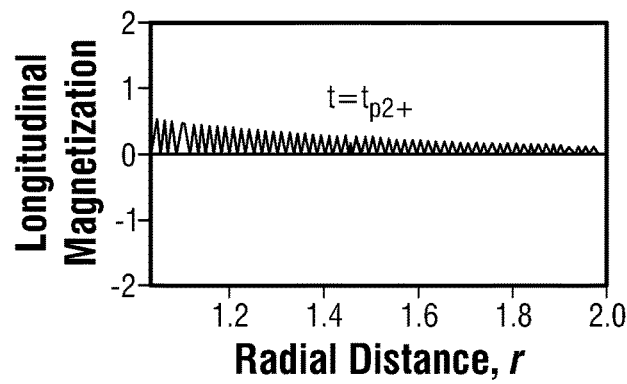

In the rotary echo pulse sequence, after the initial winding pulse, the spins are allowed to diffuse for a delay of $\Delta$, after which an unwinding pulse of duration $t_{p2}$ is applied to spatially demodulate the longitudinal magnetization. In accordance with one or more embodiments, the unwinding pulse $t_{p2}$ is of the same duration as the winding pulse so as to maximize the spatial demodulation of the spins. However, in any real and therefore imperfect system, the duration and amplitude of the winding and unwinding pulses may be different so as to maximize the spatial demodulation of the spins. After the demodulation pulse, a nominal $\pi/2$ readout pulse 1005 is applied and an FID signal is recorded immediately after the nominal $\pi/2$ pulse. A schematic of the z-magnetization at different times is illustrated in FIGS. 10(B)-10(D). The vertical axis is the magnetization and the horizontal axis is the radial coordinate. Accordingly, each curve is the radial profiles of the longitudinal magnetization at a different time. FIG. 10(B) shows the profile of the longitudinal magnetization immediately after the first modulation pulse. FIG. 10(C) shows the profile immediately before the demodulation pulse. The decay of the amplitude corresponds to the diffusion effect and this decay is the subject of the measurement. FIG. 10(D) shows the modulation immediately after the demodulation pulse. The demodulation changes the shape of the spatial profile and produces the signal to be observed. In accordance with one or more embodiments, a $\pi/2$ pulse may be combined with the second unwinding pulse, with appropriate phase cycling.

Figure 11A:
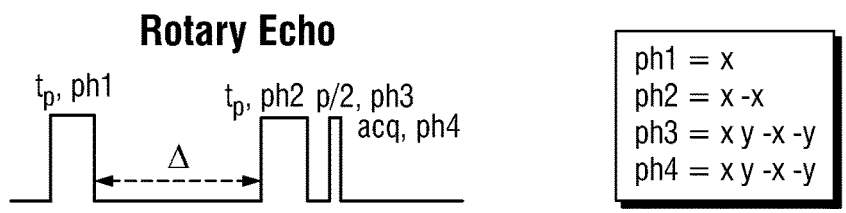
FIG. 11(A) shows a rotary echo pulse sequence in accordance with one or more embodiments.

In accordance with one or more embodiments, a diffusion measurement involves performing several FID measurements using the rotary echo pulse sequence shown in FIG. 11(A), which is similar to that shown in 10(A). The set of measurements is obtained by performing several rotary echo pulse sequences, keeping $\Delta$ fixed and a varying $t_p$. In the limit that $t_p$ is much less than $\Delta$, the detected signal S may be expressed as:

$$S \propto \int_{b_1}^{b_2} \frac{e^{-D(g\gamma t_p)^2 \Delta}}{B^2} dB, \qquad (19)$$

where $\gamma$ is proton gyromagnetic ratio. In the coaxial NMR probe shown in, for example, FIG. (1), $b = b_1 = b_2/2$, and S therefore becomes:

$$S \propto \frac{1}{2} e^{16b^4 D \gamma^2 \Delta t_p^2 \phi^2} - e^{-b^4 D \gamma^2 \Delta t_p^2 \phi^2} + \qquad (20)$$
$$b^4 D \gamma^2 t_p^2 \phi^2 E_{\frac{1}{4}}(b^4 D \gamma^2 t_p^2 \phi^2) - 8b^4 D \gamma^2 t_p^2 \phi^2 E_{\frac{1}{4}}(16 b^4 D \gamma^2 t_p^2 \phi^2),$$

where:

$$\phi = \frac{2\pi}{\mu_0 I}, \quad E_n(x) = \int_1^\infty \frac{e^{-xt} dt}{t^n},$$

and $\Delta$ is much less than $T_1$, $T_2$. In accordance with one or more embodiments, Eq. (20) can be used to extract coefficient D by fitting the signal data. The above treatment ignores $T_1$ recovery, which may be apparent in a detected signal with short $T_1$ and/or long $\Delta$.

In accordance with one or more embodiments, by increasing $t_p$ to values much larger than $\tau_{90}$, the wave vector q may be made comparable to and larger than the inverse diffusion length $(D\Delta)^{1/2}$. In this case, the attenuation of the signal due to diffusion during the interval $\Delta$, given by $e^{-q^2 D \Delta}$ becomes appreciable. In the coaxial NMR probe, the wave vector q, and therefore the attenuation is not uniform across the sample. The signal originating from the spins closer to the inner elongated conductor, where $\omega_1$ and the $B_1$ gradient are large, decays faster than the signal from spins close to the outer conductor (e.g., housing). The resulting signal for the coaxial probe is given by:

$$M_D(t_p) = \qquad (21)$$
$$M_0 e^{-\frac{\Delta}{T_1}} \int_{\omega_-}^{\omega_+} d\omega_1 \frac{\sin(\omega_1 \tau_{90})}{\omega_1^2} \cos^2(\omega_1 t_p) \exp\left\{-\frac{4\pi^2 \omega_1^4 \Delta}{\gamma^2 \mu_0^2 I^2} D t_p^2\right\}.$$

For small values of $t_p$, the $\cos^2(\omega_1 t_p)$ term leads to rapid oscillations in the signal $M_D(t_p)$. Thus, in accordance with one or more embodiments, the sensitivity may be improved by using a longer pulse duration ($t_p \gg \tau_{90}$). In this asymptotic case, the factor $\cos^2(\omega_1 t_p)$ may be replaced by its average value of $\frac{1}{2}$.

In addition, magnetization that recovers towards thermal equilibrium during the interval $\Delta$ may be spin locked during the second pulse and thus may introduce an offset $a_1$ into the detected signal shown in Eq. (9). This offset is independent of $t_p$ but is proportional to $$1 - e^{-\frac{\Delta}{T_1}}.$$

Thus, in the limit $\Delta \ll T_{190}$, $a_1$ scales as $\Delta/T_1$. Accordingly, for sufficiently long pulse duration, the diffusion kernel may be given by:

$$k_D(t_p) = a_1\left(\frac{\Delta}{T_1}\right) + e^{-\frac{\Delta}{T_1}} \int_{\omega_-}^{\omega_+} d\omega_1 \frac{\sin(\omega_1 \tau_{90})}{2\omega_1^2} \exp\left\{-\frac{4\pi^2 \omega_1^4 \Delta}{\gamma^2 \mu_0^2 I^2} D t_p^2\right\}. \qquad (22)$$

Figure 11B:
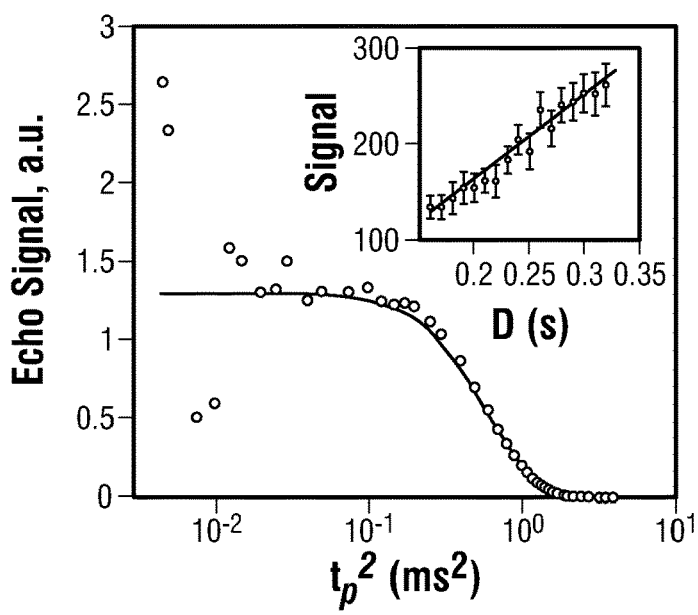
FIG. 11(B)-11(C) show rotary echo pulse sequence data acquired using a coaxial NMR probe in accordance with one or more embodiments.

Verification of the form of the offset term $a_1$ has been verified by using a composite D-$T_2$ pulse sequence, as described in more detail below in reference to FIGS. 12(A)-12(B). The result of this verification is shown in the inset of FIG. 11(B) which shows a linear dependence of the probe response on the delay $\Delta$.

In accordance with one or more embodiments, many fluids of interest have complex compositions and their diffusion response in the coaxial NMR probe is not described by a single diffusion coefficient D. In such cases, a one dimensional distribution function $f(D)$ may adequately capture the diffusion behavior resulting in the following form for the diffusion signal:

$$M_{D,asy}(t_p) = \int dD f(D) k_D(t_p). \tag{23}$$

In accordance with one or more embodiments, the distribution function $f(D)$ may be recovered from the data using a suitable numerical inversion technique.

FIG. 11(B) shows data acquired using the coaxial NMR probe of FIG. 5 filled with water and using the rotary echo sequences of FIG. 11(A) with $\Delta$ set to 160 ms, while the duration $t_p$ of the winding and unwinding pulses varied from 0-4 ms. Using Eq. (22) with D=2.53×10$^{-9}$ m$^2$/s rendered an optimal fit to the data as shown by the solid line in the FIG. 11(B). This value agrees to within 10% of the value accepted in the literature of 2.32×10$^{-9}$ m$^2$/s at 25° C. This initial oscillations in the figure originate from the above-mentioned imperfect average of cosine squared term, when the pulse length is short and are thus unrelated to molecular diffusion.

Figure 11C:
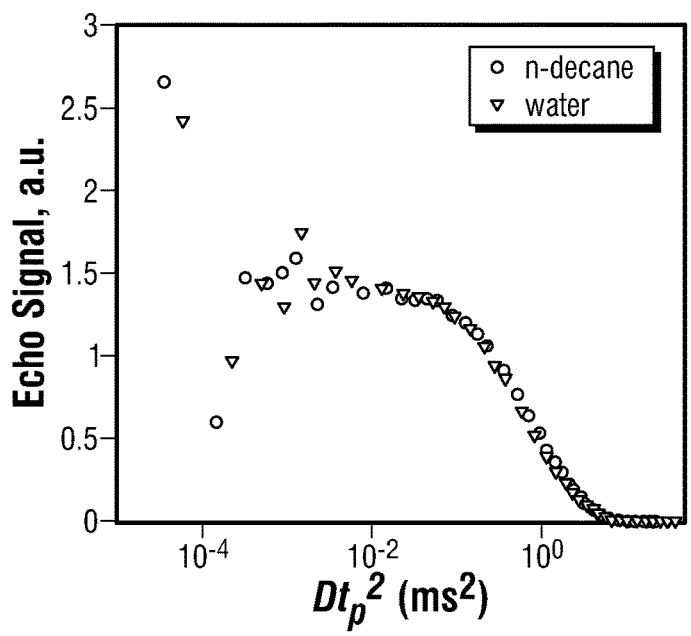

FIG. 11(C) shows the results of a measurement similar to that described above for water, but with n-decane ($C_{10}H_{22}$) as the fluid. The plot shows the diffusion data of water and n-decane as a function of D$t_p^2$, where D is the respective diffusion coefficient for the two species from the literature (2.32×10$^{-9}$ m$^2$/s for water and 1.39×10$^{-9}$ m$^2$/s for n-decane). From Eq. (22), the plotted data should be independent of fluid type in the asymptotic regime and a function of the $B_1$ distribution in the cavity. Even if $B_1$ is not known in detail, the plot of the signals for both sample as a function of D$t_p^2$ should overlap, as is the case in FIG. 11(C). Thus, the model embodied by Eq. (22) is confirmed by the results shown in FIG. 11(C).

It should be mentioned that the amplitude and spacing of the initial oscillation in the diffusion data shown in FIGS. 11(B) and 11(C) depend on the proton distribution within the cavity. Therefore, in accordance with or more embodiments, this method may be employed as a one-dimensional (1D) imaging technique to detect multiple phases (particularly gas and liquid) within the coaxial NMR probe.

In various embodiments, a composite pulse sequence is applied to the fluid sample to determine information about the fluid sample. As used herein, a composite pulse sequence is a pulse sequence that encodes for measurement of at least two NMR properties of the fluid sample (e.g., $T_1$ relaxation times, $T_2$ relaxation times, and diffusion coefficients). Such composite pulse sequences can also be referred to as two-dimensional pulse sequences. In one specific example, a composite pulse sequences includes a first component followed by a second component. The first component may include a rotary echo sequence or an inversion recovery sequence. The first component encodes for measurement of a first NMR property, such as a distribution of $T_1$ relaxation times or diffusion coefficients. The second component may include a train of CPMG pulses, which encode for measurement of a second NMR property, such as a distribution of $T_2$ relaxation times.

The composite pulse sequences can be used to generate two-dimensional maps of NMR properties. For example, the composite pulse sequences shown in FIGS. 12(A) and 13(A), respectively, can be used to generate D-$T_2$ and $T_1$-$T_2$ maps for compound mixtures for fluid typing. In accordance with one or more embodiments, the D-$T_2$ and $T_1$-$T_2$ maps may be found by measuring the two-dimensional (2D) distribution functions $f(D, T_2)$ and $f(T_1, T_2)$, respectively. $f(D, T_2)$ may be measured using a modification of the pulse sequence shown in FIG. 11(A) by replacing the FID acquisition with a train of CPMG echoes, as shown in FIG. 12(A). The pulse sequence shown in FIG. 12(A) is referred to herein as a composite rotary echo-spin echo pulse sequence. Likewise, $f(T_1, T_2)$ may be measured using a modification of the pulse sequence shown in FIG. 8(A) by replacing the FID acquisition with a train of CPMG echoes as shown in FIG. 13(A). The pulse sequence shown in FIG. 13(A) is referred to herein as a composite inversion recovery-spin echo pulse sequence. Similar to the standard CPMG sequence, the magnetization quickly reaches an asymptotic regime after the first few echoes and the responses of the coaxial NMR probe are:

$$M_{D-T_2,asy}(t_p, nt_E) = \int dD dT_2 f(D, T_2) k_D(t_p) k_{T_2}(nt_E)$$

$$\delta M_{T_1-T_2,asy}(\Delta, nt_E) = \int dT_1 dT_2 f(T_1, T_2) k_{T_1}(\Delta) k_{T_2}(nt_E). \tag{24}$$

In accordance with one or more embodiments, the following responses may also be used:

$$A_{D,T_2}(\Delta, t_p) = \iint dD dT_2 f(D, T_2) e^{-\Delta/T_1} S(D, t_p) \tag{25}$$

$$A_{T_1,T_2}(\Delta, t) = \iint dT_1 dT_2 f(T_1, T_2) e^{-\Delta/T_1} e^{-t/T_2} \tag{26}$$

where $S(D, t_p)$ is the formula on the right hand side of Eq. 20.

In accordance with one or more embodiments, the two-dimensional distribution functions $f(D, T_2)$ and $f(T_1, T_2)$ may be determined from the measured echo amplitudes of Eqs. (24)-(26). For example, a two-dimensional Fast Laplace Inversion may be used to extract the distribution functions.

Figure 12A:
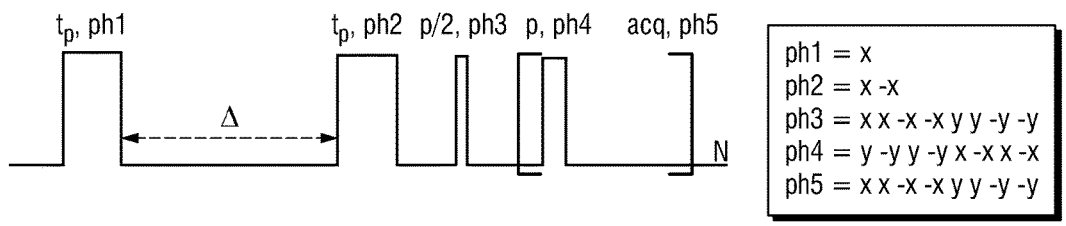
FIG. 12(A) shows a composite rotary echo-spin echo pulse sequence in accordance with one or more embodiments.
Figure 12B:
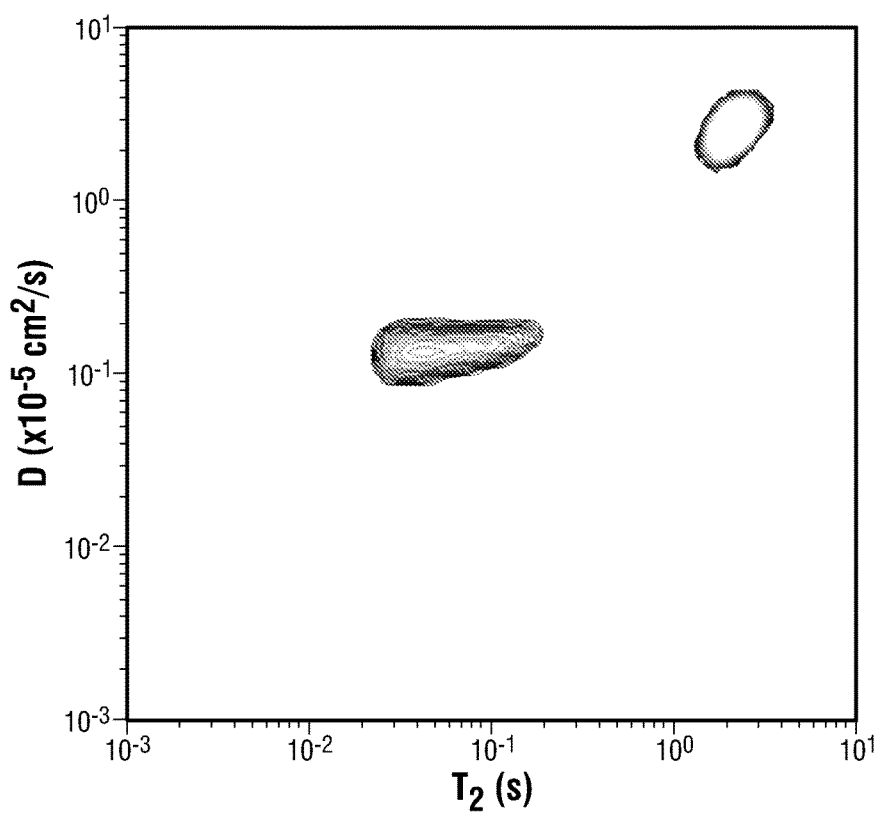
FIG. 12(B) shows composite rotary echo-spin echo pulse sequence data acquired using a coaxial NMR probe in accordance with one or more embodiments.
Figure 13A:
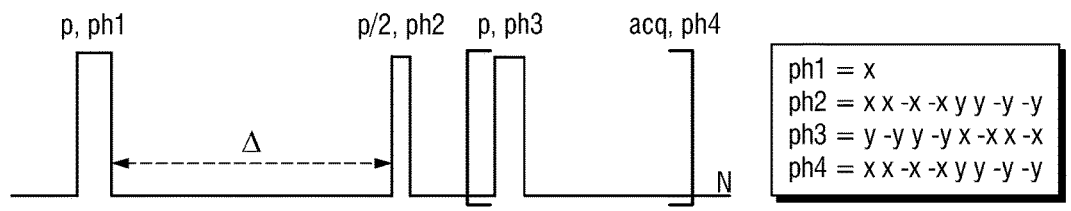
FIG. 13(A) shows a composite inversion recovery-spin echo pulse sequence in accordance with one or more embodiments.
Figure 13B:
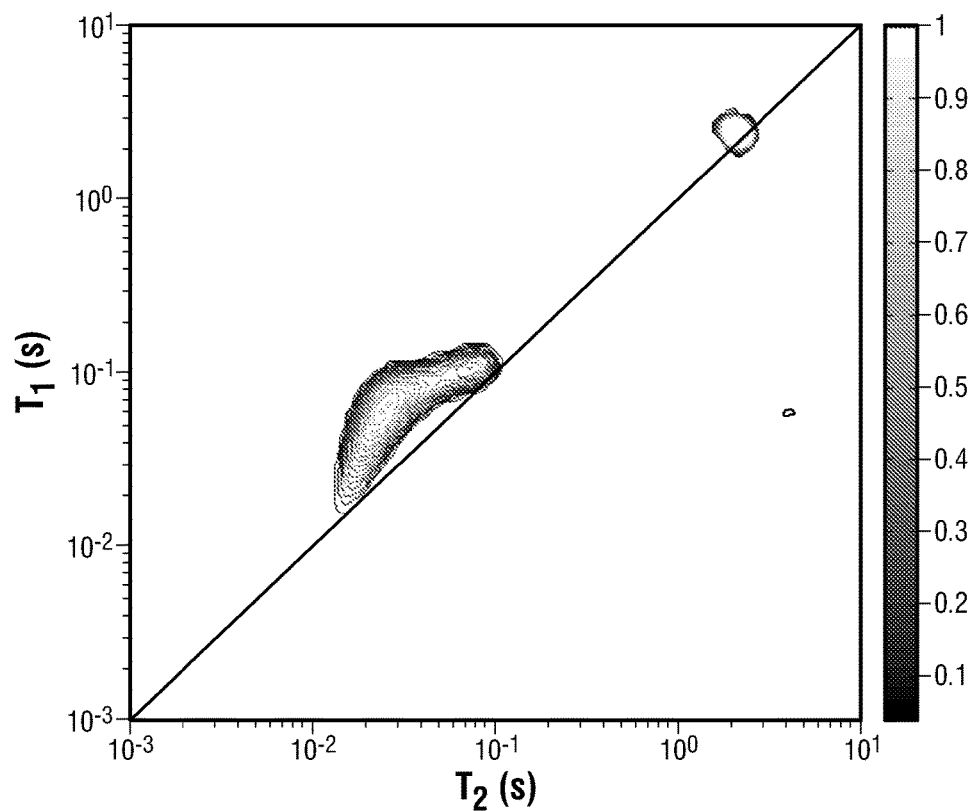
FIG. 13(B) shows composite inversion recovery-spin echo pulse sequence data acquired using a coaxial NMR probe in accordance with one or more embodiments.

FIGS. 12(B) and 13(B) show the results of measurements made using the set of pulse sequences shown in FIGS. 12(A) and 12(A), respectively. A probe like the one shown in FIG. 1 was filled with a mixture of mineral oil (CVS mineral oil usp) and water. A fast 2D Laplace inversion algorithm was used to interpret the data. Tikhonov regularization was applied to counterbalance the residual fitting errors and the known noise amplitude. More specifically, a regularization term, $\alpha$ is used to measure the desired smoothness in the distribution function and to make the inversion less ill-conditioned. An optimized $\alpha$ is such that the fitting bias is minimized and the result is stable in the presence of noise. In the plots shown in FIGS. 12(B) and 13(B), $\alpha$=1. As can be seen from FIGS. 12(B) and 13(B), water and mineral oil are clearly separated in both the $T_1$-$T_2$ and D-$T_2$ distribution functions. Strong correlations between $T_1$-$T_2$ and D-$T_2$ are also visible. The diffusion coefficient D and the $T_1$, $T_2$ relaxation times of water and mineral oil from the 2D measurements are consistent with the 1D measurements shown in FIGS. 8(C) and 9(C). While the peak for water is narrow and circular in shape, the mineral oil peak is extended in both distribution functions reflecting its more complex composition.

In accordance with one or more embodiments, the form of the diffusion kernel shown in Eq. 22 may be tested with a D-$T_2$ measurement using a set of composite rotary echo-spin echo pulse sequences in accordance with one or more embodiments. The inset of FIG. 11(B) shows the results of such an investigation. The set of pulse sequences was constructed by fixing the pulse duration of the first two pulses while increasing the delay Δ from 160 ms to 320 ms. With this value of $t_p$, the second term in Eq. 22 is vanishingly small and the signal is directly given by the offset term $a_1$. Given that $\Delta/T_1$ is less than 0.14, a linear dependence of the echo strength on Δ is expected. As seen in the inset to FIG. 11(B), this is indeed the case. Error bars in the plot are the standard error of means for the first twenty echoes at each value of Δ.

Figure 14:
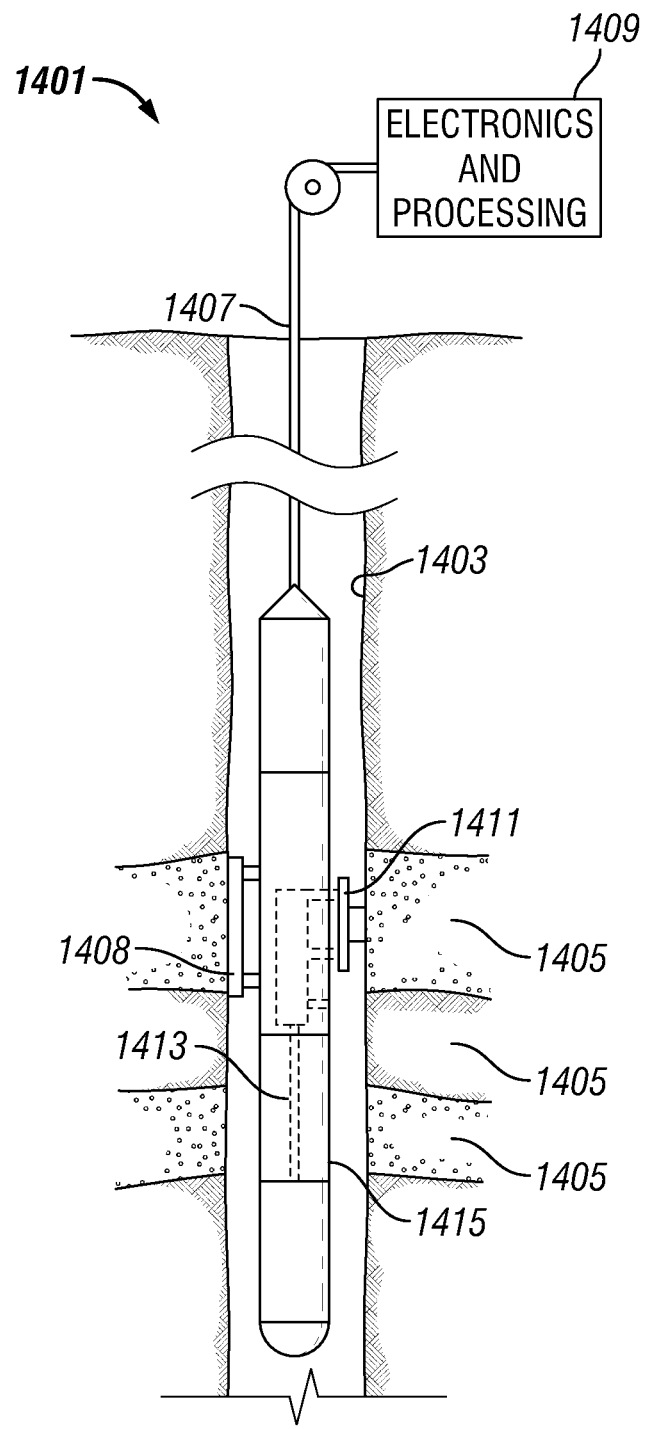
FIG. 14 shows a wellbore fluid sampling tool in accordance with one or more embodiments.

In accordance with one or more embodiments, the coaxial NMR probe may be implemented into an NMR system that may be deployed as a stand-alone analytical instrument (e.g., as a lab-based analytical instrument or as ruggedized unit for field work) or as part of a wellbore logging tool for characterizing wellbore fluids, such as a wireline tool or a logging-while-drilling (LWD) tool. For example, FIG. 14 shows a wireline tool in accordance with one or more embodiments. The wireline tool 1401 is lowered into a wellbore 1403 that traverses a formation 1405 using a cable 1407. The wireline tool 1401 is lowered down into the wellbore 1403 and makes a number of measurements of the adjacent formation at a plurality of sampling locations along the wellbore. The data from these measurements is communicated through the cable 1407 to surface equipment 1409, which may include a computer system for storing and processing the data obtained by the wireline tool (e.g., a truck or a cabin on an off-shore platform). The wireline tool 1401 may include a selectively extendable fluid admitting assembly 1411 (e.g., a probe assembly). This assembly 1411 extends into the formation 1405 and withdraws formation fluid from the formation (e.g., samples the formation). The fluid flows through the assembly 1411 and into a flow line 1413 within a housing of the tool. In accordance with one or more embodiments, a pump (not shown) may be used to withdraw the formation fluid from the formation 1405 and pass the fluid through the flow line 1413. In accordance with one or more embodiments, the NMR system described herein may be deployed as an additional module 1415 through which the flow line 1413 runs. Accordingly, the system can be used to analyze fluids within the flow line 1413 or other flow lines (not shown) within the wireline tool.

The system described herein is not limited to use with wireline tools or systems. For example, the embodiments described herein can also be used with any suitable means of conveyance, such coiled tubing. Furthermore, various embodiments of the present disclosure may also be applied in logging-while-drilling (LWD) operations, sampling-while-drilling operations, measuring-while-drilling operations, well production operations or any other operation where sampling of fluid is performed. For example, the systems and methods disclosed herein may take the form of, or be implemented within, a wellbore fluid sampling tool for determining the purity of a fluid sample (e.g., for monitoring wellbore mud contamination). In other wellbore examples, the fluid sample tool may be employed in a production line for monitoring the production of fluids. Fluids of interest may include borehole fluids, such as drilling muds, production fluids, filtrate fluids, fluids sampled directly from underground formations and/or fluids injected into underground formations.

The systems and methods disclosed herein generally relate to a system and method for the characterization of the magnetic resonance response of fluids. It will be appreciated that the systems and methods described here may also be used for performing subsurface fluid analysis in various fields, such as oilfield services, mining, water retrieval, food science, biomedical analysis, environmental monitoring, or in any other field where fluid characterization is desired.

The system and methods disclosed herein are not limited to the above-mentioned applications and these applications are included herein merely as a subset of examples. Furthermore, portions of the systems and methods may be implemented as software, hardware, firmware, or combinations thereof.

Although only a few example embodiments have been described in detail above, those skilled in the art will readily appreciate that many modifications are possible in the example embodiments without materially departing from the apparatus and method described herein. Accordingly, all such modifications are intended to be included within the scope of this disclosure.

What is claimed is:

1. A nuclear magnetic resonance (NMR) system for use in a formation, comprising:
an NMR tool including a pressure vessel housing, an elongated conductor, and a fluid admitting assembly adapted to obtain a downhole fluid sample, said pressure vessel housing comprising a fluid inlet, a fluid outlet, a central longitudinal axis, and an interior volume, wherein the housing is configured to at least partially contain the fluid sample, and said elongated conductor extends substantially along the central longitudinal axis of the housing from a first location to a second location spaced from the first location, wherein the elongated conductor is configured to generate an oscillating electromagnetic field within the interior volume of the housing, and said NMR tool is adapted to make NMR measurements of the downhole fluid sample;
a conveyance coupled to the tool for locating the NMR tool downhole; and
electronics operatively coupled to the NMR tool.

2. The NMR system of claim 1, wherein the pressure vessel housing is a metallic tube.

3. The NMR system of claim 1, wherein the pressure vessel housing and the elongated conductor form a coaxial transmission line.

4. The NMR system of claim 1, wherein the pressure vessel housing comprises a metal block having an internal passage formed therethrough and wherein an inner surface of the pressure vessel housing is an inner surface of the internal passage.

5. The NMR system of claim 1, wherein an inner diameter of the pressure vessel housing varies along the central longitudinal axis of the pressure vessel housing.

6. The NMR system of claim 5, wherein an inner surface of the pressure vessel housing forms a truncated conical shape.

7. The NMR system of claim 1, further comprising a fluid channel configured to at least partially contain the fluid sample, wherein the fluid channel comprises a conical helix and is disposed within the pressure vessel housing.

8. The NMR system of claim 1, wherein the NMR tool is part of a flow line that passes a fluid.

9. The NMR system of claim 1, wherein the fluid admitting assembly, fluid inlet and the fluid outlet of the NMR tool are coupled to the flow line and the NMR tool is configured to analyze the fluid that passes along the flow line.

10. The NMR system of claim 1, further comprising:
a power input terminal electrically coupled to the elongated conductor for providing radio frequency power to the elongated conductor; and a ground terminal electrically coupled to the pressure vessel housing such that the radio frequency power is localized within the interior volume.

11. The NMR system of claim 1, wherein the elongated conductor has a rectangular cross-section.

12. A method for analyzing a composition of a downhole fluid sample, the method comprising:
introducing the downhole fluid sample into a sample volume of a coaxial nuclear magnetic resonance (NMR) probe having a pressure vessel housing with a central longitudinal axis and an elongated conductor extending substantially along the central longitudinal axis of the housing from a first location to a second location spaced from the first location;
applying a magnetic field to generate a magnetization within the fluid sample, wherein the magnetic field is applied along a bias magnetization direction;
applying a composite pulse sequence to the elongated conductor extending through the sample volume within the coaxial probe to generate an oscillating magnetic field gradient within the fluid sample;
using the elongated conductor to receive a magnetic resonance signal from the fluid sample; and
analyzing the received magnetic resonance signal to determine information about the fluid sample.

13. The method of claim 12, wherein analyzing the received magnetic resonance signal comprises determining a two-dimensional distribution function for a first and a second property of the fluid sample using the magnetic resonance signal.

14. The method of claim 13, wherein the first property is a diffusion coefficient D and the second property is a spin-spin relaxation time $T_2$.

15. The method of claim 13, wherein the first property is a spin-lattice relaxation time $T_1$ and the second property is a spin-spin relaxation time $T_2$.

16. The method of claim 12, wherein the longitudinal conductor has a rectangular cross-section.

17. The method of claim 12, wherein the composite pulse sequence comprises a composite free induction decay-spin echo pulse sequence.

18. The method of claim 12, wherein the composite pulse sequence comprises applying a composite rotary echo-spin echo pulse sequence.

19. A method for analyzing a composition of a downhole fluid sample, the method comprising:
locating a coaxial nuclear magnetic resonance (NMR) downhole tool in a wellbore traversing a formation;
flowing the downhole fluid sample into a sample volume through a fluid inlet of the (NMR) downhole tool;
applying a magnetic field to generate a magnetization within the fluid sample, wherein the magnetic field is applied along a bias magnetization direction;
applying a pulse sequence to an elongated conductor extending through the sample volume within the coaxial probe to generate an oscillating magnetic field within the fluid sample;
using the elongated conductor to receive a magnetic resonance signal from the fluid sample;
flowing the fluid sample out of the sample volume through an outlet of the coaxial NMR downhole tool; and
analyzing the received magnetic resonance signal to determine information about the fluid sample.

20. A method for analyzing a composition of a fluid sample, the method comprising:
flowing the fluid sample into a sample volume through a fluid inlet of a coaxial nuclear magnetic resonance (NMR) probe;
applying a magnetic field to generate a magnetization within the fluid sample, wherein the magnetic field is applied along a bias magnetization direction;
applying a free induction decay pulse sequence that includes a nominal π pulse followed by a nominal π/2 pulse to an elongated conductor extending through the sample volume within the coaxial probe to generate an oscillating magnetic field within the fluid sample;
using the elongated conductor to receive a magnetic resonance signal from the fluid sample after applying the nominal π/2 pulse;
flowing the fluid sample out of the sample volume through an outlet of the coaxial NMR probe; and
analyzing the received magnetic resonance signal to determine information about the fluid sample,
wherein receiving a magnetic resonance signal from the fluid sample comprises receiving a free induction decay signal from the fluid sample after applying the nominal π/2 pulse.

21. A method for analyzing a composition of a fluid sample, the method comprising:
flowing the fluid sample into a sample volume through a fluid inlet of a coaxial nuclear magnetic resonance (NMR) probe;
applying a magnetic field to generate a magnetization within the fluid sample, wherein the magnetic field is applied along a bias magnetization direction;
applying a spin echo pulse sequence that includes a nominal π/2 pulse followed by a series of nominal 7C pulses to an elongated conductor extending through the sample volume within the coaxial probe to generate an oscillating magnetic field within the fluid sample;
flowing the fluid sample out of the sample volume through an outlet of the coaxial NMR probe; and
analyzing the received magnetic resonance signal to determine information about the fluid sample,
wherein receiving a magnetic resonance signal from the fluid sample comprises receiving a plurality of spin echo signals from the fluid sample after applying each nominal π pulse.

22. A method for analyzing a composition of a fluid sample, the method comprising:
flowing the fluid sample into a sample volume through a fluid inlet of a coaxial nuclear magnetic resonance (NMR) probe;
applying a magnetic field to generate a magnetization within the fluid sample, wherein the magnetic field is applied along a bias magnetization direction;
applying a pulse sequence to an elongated conductor extending through the sample volume within the coaxial probe to generate an oscillating magnetic field within the fluid sample;
using the elongated conductor to receive a magnetic resonance signal from the fluid sample;
flowing the fluid sample out of the sample volume through an outlet of the coaxial NMR probe; and
analyzing the received magnetic resonance signal to determine information about the fluid sample,
wherein applying the pulse sequence comprises applying a rotary echo pulse sequence that comprises
applying the oscillating magnetic field for a first duration to $t_{p1}$ generate a spatial modulation of the magnetization,
waiting a duration Δ, pulsing the oscillating magnetic field for a second duration $t_{p2}$, and applying a nominal π/2 pulse, and wherein receiving a magnetic resonance signal from the fluid sample comprises receiving a free induction decay signal after applying the nominal π/2 pulse.

23. A wellbore logging tool comprising:

an assembly for withdrawing formation fluid from a formation; and a flow line for passing the formation fluid through the tool, wherein the flow line comprises a nuclear magnetic resonance (NMR) probe configured to analyze the formation fluid that passes through the flow line, wherein the NMR probe comprises:

a pressure vessel housing defining a central longitudinal axis and an interior volume, wherein the housing is configured to at least partially contain the formation fluid; and an elongated conductor extending substantially along the central longitudinal axis of the housing from a first location to a second location spaced from the first location, wherein the elongated conductor is configured to generate an oscillating electromagnetic field within the interior volume.

* * * * *